United States Patent

Whittle et al.

[11] Patent Number: 5,104,878
[45] Date of Patent: Apr. 14, 1992

[54] 1-PHENYL-6-ONE-PYRIMIDINE DERIVATIVES

[75] Inventors: Alan J. Whittle, Twyford; Trevor R. Perrior, Barkham; Raymond L. Sunley, Twyford, all of United Kingdom

[73] Assignee: Imperial Chemical Industries PLC, London, United Kingdom

[21] Appl. No.: 506,167

[22] Filed: Apr. 9, 1990

[30] Foreign Application Priority Data

Apr. 17, 1989 [GB] United Kingdom ............. 8908638

[51] Int. Cl.$^5$ ............... C07D 239/36; C07D 239/38; A01N 43/54
[52] U.S. Cl. ........................ 514/269; 514/272; 514/274; 544/299; 544/301; 544/302; 544/303; 544/309; 544/311; 544/312; 544/313; 544/314; 544/319; 544/321
[58] Field of Search ............... 514/269, 272, 274; 544/299, 301, 302, 303, 309, 311, 312, 313, 314, 319, 321

[56] References Cited

U.S. PATENT DOCUMENTS

| | | | |
|---|---|---|---|
| 3,185,689 | 5/1965 | Ruschig et al. | 260/251 |
| 3,235,358 | 2/1966 | Soboczenski | 71/2.5 |
| 3,254,082 | 5/1966 | Loux et al. | 260/260 |
| 3,291,592 | 12/1966 | Evans | 71/2.5 |
| 3,580,913 | 5/1971 | Lutz | 260/260 |
| 3,823,135 | 7/1974 | Pilgram et al. | 260/251 R |
| 3,869,457 | 3/1975 | Lutz et al. | 544/319 |
| 4,145,546 | 3/1979 | Brown et al. | 544/310 |
| 4,147,528 | 4/1979 | McNulty et al. | 71/92 |

FOREIGN PATENT DOCUMENTS

| | | |
|---|---|---|
| 888730 | 12/1971 | Canada ............... 260/255 |
| 0129528 | 12/1984 | European Pat. Off. |
| 0180298 | 5/1986 | European Pat. Off. |
| 0273409 | 7/1988 | European Pat. Off. |
| 0338686 | 10/1989 | European Pat. Off. |
| 1035091 | 7/1966 | United Kingdom . |
| 1035092 | 7/1966 | United Kingdom . |
| 1035097 | 7/1966 | United Kingdom . |
| 1035098 | 7/1966 | United Kingdom . |
| 1240392 | 7/1971 | United Kingdom . |
| 1447108 | 8/1976 | United Kingdom . |
| 2130214 | 5/1984 | United Kingdom . |

OTHER PUBLICATIONS

Chemical Abstracts, vol. 105, No. 23, Dec. 8, 1986, p. 566, Abstract No. 208595s, Columbia, Ohio, U.S.; & JP-A-61 083 146 (Nippon Soda Co., Ltd.), Apr. 26, 1986.

Primary Examiner—John M. Ford
Attorney, Agent, or Firm—Cushman, Darby & Cushman

[57] ABSTRACT

A compound of formula (I):

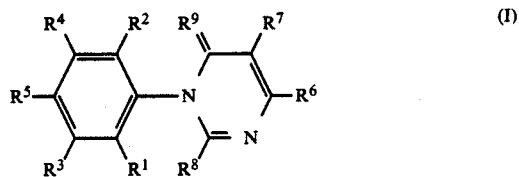

wherein $R^1$ and $R^2$ are independently selected from hydrogen, halogen, haloalkyl, alkoxy or nitro, provided that $R^1$ and $R^2$ are not both nitro; $R^3$ and $R^4$ are independently selected from hydrogen, halogen, alkyl or cycloalkyl; $R^5$ is halogen, nitro, haloalkyl, haloalkoxy or $-S(O)_nR^{10}$; $R^6$ is halogen, nitro, haloalkyl, haloalkoxy or $-S(O)_nR^{10}$; $R^7$ is hydrogen, halogen, hydroxyalkyl, cyano, nitro, alkoxy, $-S(O)_nR^{10}$, $NR^{11}R^{12}$, haloalkyl or formyl; $R^8$ is hydrogen, halogen, $NR^{11}R^{12}$, alkyl, cycloalkyl or $S(O)_n R^{10}$; and $R^9$ is oxygen or sulphur; where n is 0, 1 or 2; and $R^{10}$ is alkyl, haloalkyl or cycloalkyl; and $R^{11}$ and $R^{12}$ are independently selected from hydrogen, alkyl or cycloalkyl or $R^{11}$ and $R^{12}$ together with the nitrogen to which they are attached form a heterocyclic group; provided that when $R^5$ is trifluoromethyl at least one of the following applies:

(i) $R^1$ or $R^2$ is haloalkyl or alkoxy;
(ii) $R^3$ or $R^4$ are alkyl or cycloalkyl;
(iii) $R^6$ is haloalkoxy, nitro or $-S(O)_nR^{10}$;
(iv) $R^7$ is nitro, hydroxyakyl, alkoxy, $S(O)_nR^{10}$, $NR^{11}R^{12}$, formyl or haloalkyl;
(v) $R^8$ is other than hydrogen;
(vi) $R^9$ is sulphur; and further provided that (a) $R^1$, $R^2$, $R^3$ and $R^4$ are not all fluorine and (b) when $R^5$ is chlorine, $R^1$ and $R^2$ are both halogen.

16 Claims, No Drawings

1-PHENYL-6-ONE-PYRIMIDINE DERIVATIVES

The present invention relates to novel phenyl pyrimidinone derivatives which have insecticidal activity, to processes for their preparation and to their use as insecticides.

European Patent Publication No. 0338686 discloses compounds of formula (A):

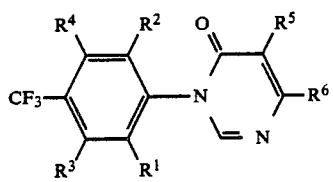

wherein $R^1$ and $R^2$ are independently selected from halogen or nitro; $R^3$ and $R^4$ are independently selected from hydrogen or halogen; $R^5$ is hydrogen, halogen or cyano; and $R^6$ is halogen or haloalkyl; provided that $R^1$, $R^2$, $R^3$ and $R^4$ are not all fluorine.

According to the present invention there is provided a compound of formula (I):

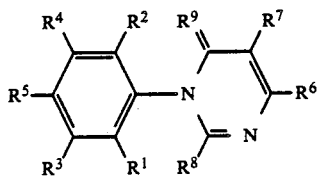

wherein $R^1$ and $R^2$ are independently selected from hydrogen, halogen, haloalkyl, alkoxy or nitro, provided that $R^1$ and $R^2$ are not both nitro; $R^3$ and $R^4$ are independently selected from hydrogen, halogen, alkyl or cycloalkyl; $R^5$ is halogen, nitro, haloalkyl, haloalkoxy or —S(O)$_n$R$^{10}$; $R^6$ is halogen, nitro, haloalkyl, haloalkoxy or —S(O)$_n$R$_{10}$; $R^7$ is hydrogen, alkyl, halogen, hydroxyalkyl, cyano, nitro, alkoxy, —S(O)$_n$R$^{10}$, NR$^{11}$R$^{12}$, haloalkyl or formyl; $R^8$ is hydrogen, halogen, NR$^{11}$R$^{12}$, alkyl, cycloalkyl or S(O)$_n$R$^{10}$; $R^9$ is oxygen or sulphur; where n is 0, 1 or 2; $R^{10}$ is alkyl, haloalkyl or cycloalkyl; $R^{11}$ and $R^{12}$ are independently selected from hydrogen, alkyl, cycloalkyl or $R^{11}$ and $R^{12}$ together with the nitrogen to which they are attached form a heterocyclic group; provided that when $R^5$ is trifluoromethyl at least one of the following applies:

(i) $R^1$ or $R^2$ is haloalkyl or alkoxy;
(ii) $R^3$ or $R^4$ are alkyl or cycloalkyl;
(iii) $R^6$ is haloalkoxy, nitro or —S(O)$_n$R$^{10}$,
(iv) $R^7$ is alkyl, nitro, hydroxyalkyl, alkoxy, S(O)$_n$R$^{10}$, NR$^{11}$R$^{12}$, formyl or haloalkyl;
(v) $R^8$ is other than hydrogen;
(vi) $R^9$ is sulphur; and further provided that (a) $R^1$, $R^2$, $R^3$ and $R^4$ are not all fluorine and (b) that when $R^5$ is chlorine, $R^1$ and $R^2$ are both halogen.

Suitable halogen groups for $R^1$, $R^2$, $R^3$, $R^4$, $R^5$, $R^6$, $R^7$ and $R^8$ include fluoro, chloro, bromo or iodo.

The term "alkyl" is used herein includes straight or branched chain alkyl groups, preferably containing up to 6 carbon atoms. This applies also to alkyl moieties contained in "haloalkyl" groups. The term "cycloalkyl" used herein refers to a carbocyclic ring suitably having from 3 to 10 and preferably from 3 to 7 carbon atoms in the ring. The cycloalkyl group is preferably cyclopropyl, cyclopentyl or cyclohexyl.

Suitable haloalkyl groups for $R^1$, $R^2$, $R^5$, $R^6$, $R^7$ and $R^{10}$ are $C_1$-$C_4$ alkyl groups substituted with chlorine, fluorine or bromine or iodine. Such groups include di- and trihalomethyl groups, in particular trifluoromethyl, and pentahaloethyl groups, in particular pentafluoroethyl. Such groups may also be substituted with two or more different halogens.

Suitable alkoxy groups for $R^1$, $R^2$ and $R^7$ include $C_1$-$C_4$ alkoxy groups, in particular methoxy and ethoxy.

Suitable haloalkoxy groups for $R^5$ and $R^6$ include $C_1$-$C_4$ alkoxy groups substituted with one or more halogen atoms which may be the same or different, for example, fluorine, chlorine, bromine, or iodine.

Suitable hydroxyalkyl groups for $R^7$ include hydroxy-$C_1$-$C_4$ alkyl groups.

Preferably $R^1$ and $R^2$ are fluorine, chlorine, bromine, nitro, trifluoromethyl or methoxy.

Preferably $R^3$ and $R^4$ are hydrogen or methyl.

Preferably $R^5$ is trifluoromethyl, pentafluoroethyl, trifluoromethylthio, iodine, bromine, chlorine, trifluoromethoxy or methylthio.

Preferably $R^6$ is trifluoromethyl or pentafluoroethyl.

Preferably $R^7$ is hydrogen, trifluoromethylthio, methylthio, halogen, or methyl.

Preferably $R^8$ is hydrogen, methyl, NH$_2$ or methylthio.

Preferably $R^9$ is oxygen.

Examples of compounds of formula (I) are set out in Table I below.

TABLE I

| CPD NO. | $R^1$ | $R^2$ | $R^3$ | $R^4$ | $R^5$ | $R^6$ | $R^7$ | $R^8$ | $R^9$ |
|---|---|---|---|---|---|---|---|---|---|
| 1 | Cl | Cl | H | CH$_3$ | CF$_3$ | CF$_3$ | H | H | O |
| 2 | CF$_3$ | NO$_2$ | H | H | CF$_3$ | CF$_3$ | H | H | O |
| 3 | Cl | Cl | H | H | Cl | CF$_3$ | H | H | O |
| 4 | Cl | Cl | H | H | I | CF$_3$ | H | H | O |
| 5 | Cl | Cl | H | H | NO$_2$ | CF$_3$ | H | H | O |
| 6 | Cl | Cl | H | H | Br | CF$_3$ | H | H | O |
| 7 | Cl | OCH$_3$ | H | H | CF$_3$ | CF$_3$ | H | H | O |
| 8 | CF$_3$ | NO$_2$ | H | H | CF$_3$ | CF$_3$ | Br | H | O |
| 9 | CF$_3$ | Cl | H | H | CF$_3$ | CF$_3$ | H | H | O |
| 10 | CF$_3$ | Cl | H | H | CF$_3$ | CF$_3$ | Br | H | O |
| 11 | CF$_3$ | Br | H | H | CF$_3$ | CF$_3$ | H | H | O |
| 12 | CF$_3$ | Br | H | H | CF$_3$ | CF$_3$ | Br | H | O |
| 13 | Cl | NO$_2$ | H | H | OCF$_3$ | CF$_3$ | H | H | O |
| 14 | Cl | Cl | H | H | OCF$_3$ | CF$_3$ | H | H | O |
| 15 | Cl | Br | H | H | OCF$_3$ | CF$_3$ | H | H | O |
| 16 | Cl | Cl | H | H | OCF$_3$ | CF$_3$ | Br | H | O |
| 17 | Cl | NO$_2$ | H | H | OCF$_3$ | C$_2$F$_5$ | H | H | O |
| 18 | Cl | Cl | H | H | OCF$_3$ | C$_2$F$_5$ | H | H | O |

TABLE I-continued

| CPD NO. | R¹ | R² | R³ | R⁴ | R⁵ | R⁶ | R⁷ | R⁸ | R⁹ |
|---|---|---|---|---|---|---|---|---|---|
| 19 | Cl | Cl | H | H | C₂F₅ | CF₃ | H | H | O |
| 20 | Cl | Cl | H | H | C₂F₅ | C₂F₅ | H | H | O |
| 21 | Cl | Cl | H | H | C₂F₅ | CF₃ | Br | H | O |
| 22 | Cl | Cl | H | H | C₂F₅ | C₂F₅ | Br | H | O |
| 23 | Cl | Cl | H | H | CF₃ | CF₃ | H | SCH₃ | O |
| 24 | Cl | Cl | H | H | CF₃ | CF₃ | H | SOCH₃ | O |
| 25 | Cl | Cl | H | H | CF₃ | CF₃ | H | SO₂CH₃ | O |
| 26 | Cl | Cl | H | H | CF₃ | CF₃ | H | NH₂ | O |
| 27 | Cl | Cl | H | H | CF₃ | CF₃ | H | NHCH₃ | O |
| 28 | Cl | Cl | H | H | CF₃ | CF₃ | H | N(CH₃)₂ | O |
| 29 | Cl | Cl | H | H | CF₃ | CF₃ | H | CH₃ | O |
| 30 | Cl | Cl | H | H | CF₃ | CF₃ | SCH₃ | H | O |
| 31 | Cl | NO₂ | H | H | CF₃ | CF₃ | SCH₃ | H | O |
| 32 | Cl | NO₂ | H | H | CF₃ | CF₃ | SOCH₃ | H | O |
| 33 | Cl | Cl | H | H | CF₃ | CF₃ | SO₂CH₃ | H | O |
| 34 | Cl | NO₂ | H | H | CF₃ | CF₃ | SCF₃ | H | O |
| 35 | Cl | NO₂ | H | H | CF₃ | CF₃ | CHO | H | O |
| 36 | Cl | Cl | H | H | CF₃ | CF₃ | OC₂H₅ | H | O |
| 37 | Cl | NO₂ | H | H | CF₃ | CF₃ | OC₂H₅ | H | O |
| 38 | Cl | NO₂ | H | H | CF₃ | CF₃ | CHF₂ | H | O |
| 39 | Cl | Cl | H | H | CF₃ | CF₃ | CH₃ | H | O |
| 40 | Cl | NO₂ | H | H | CF₃ | CF₃ | CH₃ | H | O |
| 41 | Cl | Cl | H | H | CF₃ | CF₃ | NH₂ | H | O |
| 42 | Cl | NO₂ | H | H | CF₃ | CF₃ | NO₂ | H | O |
| 43 | Cl | Cl | H | H | SCF₃ | CF₃ | H | H | O |
| 44 | Cl | Cl | H | H | SCH₃ | CF₃ | H | H | O |
| 45 | Cl | NO₂ | H | H | CF₃ | CF₃ | CH₂OH | H | O |
| 46 | Cl | Cl | H | H | CF₃ | CF₃ | HC(OH)(CH₃) | H | O |
| 47 | Cl | Cl | H | H | CF₃ | CF₃ | H | H | S |
| 48 | Cl | NO₂ | H | H | CF₃ | CF₃ | CH(F)(CH₃) | H | O |
| 49 | Cl | Br | H | H | OCF₃ | C₂F₅ | H | H | O |

Compounds of formula (I) can be prepared by reacting a compound of formula (II):

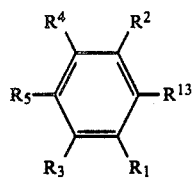

(II)

wherein R¹, R², R³, R⁴ and R⁵ are as defined in relation to formula (I) and R¹³ is a leaving group, provided that R¹ and R² can both be nitro, with a compound of formula (III):

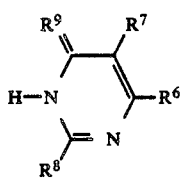

(III)

wherein R⁶, R⁷, R⁹ are as defined in relation to formula (I) and R⁸ is hydrogen. Thereafter, if desired (a) converting a group R¹-R⁷ to a different such group; and/or (b) converting compounds where R⁹ is oxygen to compounds where R⁹ is sulphur.

The reaction is suitably carried out in the presence of a solvent and a base. The base may be for example an alkali metal hydride, an alkali metal alkoxide or an alkali metal carbonate, and the solvent may be a hydrocarbon solvent, such as petroleum ether, or toluene, or an ether such as tetrahydrofuran, or an aprotic polar solvent such as dimethylformamide or dimethylacetamide, or an etherial solvent, such as diglyme.

Suitable leaving groups R¹³ include halo groups such as fluoro, chloro, bromo, iodo or trifluoromethylsulphonyloxy or methylsulphonyloxy.

If necessary an appropriate catalyst such as a crown ether, copper, or potassium fluoride can be added depending upon the precise nature of R¹³.

Conversion of a group R¹-R⁸ to a different such group or R⁹ from oxygen to sulphur, may be carried out by conventional methods. In particular compounds of formula (I) wherein any one or more of R¹, R², R⁵, R⁶ and/or R⁷ is nitro can be converted into the corresponding compound of formula (I) wherein any one or more of R¹, R², R⁵, R⁶ or R⁷ is halo by reduction of the nitro group to an amino group to form a compound of formula (IV):

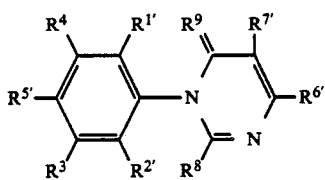

(IV)

wherein $R^3$, $R^4$, $R^8$ and $R^9$ are as defined in relation to formula (I) and $R^{1'}$, $R^{2'}$, $R^{5'}$, $R^{6'}$ and $R^{7'}$ are amino or are equivalent to $R^1$, $R^2$, $R^5$, $R^6$ and $R^7$ as defined in relation to formula (I) respectively provided that at least one of $R^{1'}$, $R^{2'}$ $R^{5'}$, $R^{6'}$ or $R^{7'}$ is amino; and thereafter converting the amino group $R^{1'}$, $R^{2'}$, $R^{4'}$, $R^{6'}$ and/or $R^{7'}$ to halo.

Certain compounds of formula (IV) are novel and as such form a further aspect of the invention.

Reduction of the nitro group to form a compound of formula (IV) can be carried out by reacting the compound with a reducing agent such as stannous chloride in acid conditions, for example, in a solution in concentrated hydrochloric acid. Alternatively, the reduction may be carried out using reduced iron powder in a hydroxylic solvent, such as isopropanol in the presence of an acid catalyst, for example, hydrochloric acid. Moderate temperatures of from 2° to 90° C. are suitably employed.

Subsequent conversion of the amine to a halogen may be carried out by reaction with t-butylnitrite and a copper halide salt such as copper (I) iodide. This step is suitably carried out in an organic solvent such as acetonitrile at low temperatures of from −20° C. to +20° C. preferably at about 0° C.

Further conversion of compounds of formula (I) where $R^1$–$R^8$ are as previously defined for formula (I), and one or both of $R^1$ and $R^2$ is nitro and $R^9$ is oxygen to the corresponding compounds where $R^1$ and/or $R^2$ are halogen can be achieved by reaction with an alkali metal halide, such as lithium chloride, in a polar solvent, such as diglyme.

Compounds of formula (I) where $R^7$ is hydrogen may be converted to compounds of formula (I) where $R^7$ is halogen by conventional methods, for example, bromination with bromine in acetic acid, preferably in the presence of a base such as sodium acetate, or to compounds where $R^7$ is nitro by reaction with nitrating agents, such as nitronium tetrafluoroborate, in a polar solvent, such as acetonitile or sulpholane.

Compounds of formula (I), (II) or (III) where any combination of $R^5$–$R^8$ are —$SR^{10}$ can be converted to the corresponding compounds of formula (I), (II) or (III) where any combination of $R^5$–$R^8$ are —$SOR^{10}$ or —$SO_2R^{10}$ by reaction with an oxidising agent such as m-chloroperbenzoic acid.

Conversion of compounds of formula (I) or (III) where $R^7$ is formyl to difluoromethyl, or where $R^7$ is 1-hydroxyalkyl to 1-fluoroalkyl can be achieved by reaction with diethylamino sulphur trifluoride.

Compounds of formula (I) where $R^5$ or $R^7$ is trifluoromethylthio can be prepared from the corresponding halogen derivatives, preferably where $R^5$ or $R^7$ is iodine, by reaction with trifluoromethylthio copper.

Conversion of $R^9$ from oxygen to sulphur in compounds of formula (I) may be carried out by reaction with a thionating agent, such as Lawesson's reagent or $P_2S_5$, suitably at reflux.

Compounds of formula (I) where $R^1$ and $R^2$ are halogen, $R^3$ and $R^4$ are hydrogen or methyl, $R^5$ is halogen, haloalkyl, haloalkoxy or $S(O)_nR^{10}$, $R^6$ is haloalkyl, $R^7$ is hydrogen or alkyl, $R^8$ is alkyl and $R^9$ is oxygen may suitably be prepared by reacting a compound of formula (I) where $R^1$ to $R^7$ are as above and is hydrogen with a lower dialkylamine in the presence of a suitable hydroxylic solvent, for example methanol or ethanol suitably at a temperature of ambient to 80° C. to give a compound of formula (VI):

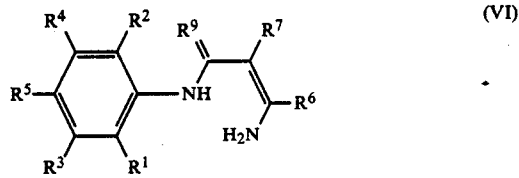

(VI)

where $R^1$, $R^2$, $R^3$, $R^4$, $R^5$, $R^6$, $R^7$ and $R^9$ are as herein before defined, followed by reaction with an acylating agent, such as an acyl chloride, acid anhydride or activated acyl ester with a base, such as a tertiaryalkylamine, e.g. triethylamine, in the presence of an inert solvent, for example, toluene, dimethylformamide or dichloromethane, to give a compound of formula (I) where $R^8$ is derived from the acylating agent. The acylation reaction is suitably carried out at a temperature of 0° C. to 30° C. The ring closure of the acylated compound derived from formula (VI) may happen spontaneously in the reaction mixture or in the presence of a catalytic amount of an organic acid, such as p-toluene sulphonic acid or an inorganic acid, such as hydrochloric acid or sulphuric acid. Thereafter, if desired, (a) where $R^7$ is hydrogen, it can be converted to a halogen; and/or (b) $R^9$ can be converted to sulphur.

Compounds of formula (I) where $R^1$ and $R^2$ are halogen, $R^3$ and $R^4$ are hydrogen or methyl, $R^5$ is halogen, haloalkyl, haloalkoxy or —$S(O)_nR^{10}$, $R^6$ is haloalkyl, $R^7$ is hydrogen, $R^8$ is alkylthio and $R^9$ is oxygen and are suitably prepared by reaction of a compound of formula (VII):

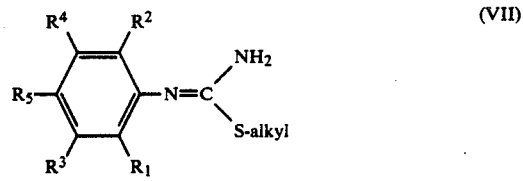

(VII)

where $R^1$, $R^2$, $R^3$, $R^4$ and $R^5$ are as defined herein with a compound of formula (VIII):

$$R^6-C\equiv C-CO_2\text{-alkyl} \qquad (VIII)$$

where $R^6$ is as previously defined, in the presence of a base, such as a metal hydride e.g. sodium or potassium hydride and a dipolar aprotic solvent such as dimethylformamide, dimethylsulphoxide or N-methyl pyrollidone. The reaction is suitably carried out from 0° C. to ambient temperature. Conversion to the compounds or formula (I) where $R^7$ is halogen can be carried out by conventional methods.

The compounds of formula (VII) and (VIII) may be obtained by conventional methods.

Compounds of formula (I) where $R^1$ and $R^2$ are halogen, $R^3$ and $R^4$ are hydrogen or methyl, $R^5$ is halogen, haloalkyl, haloalkoxy or —$S(O)_2R^{10}$, $R^6$ is haloalkyl, $R^7$ is hydrogen or halogen and $R^8$ is alkylsulphonyl are suitably prepared by reaction of a compound of formula (I) as herein defined where $R^8$ is alkylthio with an oxidising agent, for example, m-chloroperbenzoic acid, in a halogenated solvent, such as chloroform, carbon tetrachloride or dichloromethane. The compound where $R^8$ is alkylsulphinyl is an intermediate in this reaction and can be isolated by conventional methods when an appropriate amount of the oxidising agent is used.

Compounds of formula (I) where $R^1$ and $R^2$ are halogen, $R^3$ and $R^4$ are hydrogen or methyl, $R^5$ is halogen, haloalkyl, haloalkoxy or $-S(O)_nR^{10}$, $R^6$ is haloalkyl and $R^7$ is hydrogen or halogen and $R^8$ is $NR^{11}R^{12}$, can suitably be prepared from a corresponding compound of formula (I) where $R^8$ is alkylsulphonyl, by (a) reaction with a suitable nucleophilic reagent, for example ammonia or a primary or secondary alkylamine such as dimethylamine or methylamine, in the presence of a hydroxylic solvent, such as tertiary butanol, suitably at a temperature of 0° C. to 80° C., or (b) by fusion with ammonium acetate or alkylated ammonium acetate, suitably at a temperature of 100° to 140° C.

Certain compounds of formula (II) and (III) are known compounds. Others are novel compounds and these form a further aspect of the invention. These compounds can be prepared from known compounds by conventional methods. The conversion of groups $R^1$-$R^8$ to different such groups may be carried out on the compounds of formula (II) and (III) prior to coupling together to give a compound of formula (I), if desired. This may produce novel intermediates for example where nitro groups $R^1$, $R^2$, $R^5$, $R^6$ and $R^7$ are converted to amino groups prior to halogenation. The methods for a conversion of this type are suitably the same as described above in relation to the equivalent conversions on the compounds of formula (I).

The following compounds of formula (II), 6-nitro-2,4-bis (trifluoromethyl) bromobenzene, 2-chloro-4-trifluoromethoxy-6-nitroaniline, 3,4-dichloro-5-nitro-trifluoromethoxybenzene, 3-chloro-4-fluoro-5-nitro-trifluoromethoxybenzene, 3,5-dichloro-4-fluoro-pentafluoroethylbenzene are novel and form a further aspect of the invention. These compounds can be prepared by the specific methods defined in the preparations.

Compounds of formula (III) where $R^7$ is alkyl, $S(O)_nR^{10}$, alkoxy, formyl, or hydroxyalkyl, $R^8$ is hydrogen, $R^9$ is oxygen, and $R^6$ is haloalkyl are novel and form a further aspect of the invention.

Compounds of formula (III) can be prepared by general methods known in the art such as (a) condensation of a beta-ketoester of formula (IX):

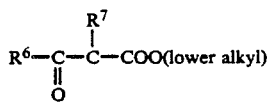

(IX)

with thiourea or an S-alkyl isothiourea to give a compound of formula (X):

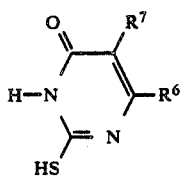

(X)

and subsequent desulphurisation with Raney nickel to give a compound of formula (III) where $R^8$ is hydrogen; or (b) condensation of the beta-ketoester with formamidine to give the compound of formula (III) where R8 is hydrogen; or (c) halogenation of 4-($R^6$)-pyrimidin-6-one by conventional methods to give 5-halo-4-($R^6$)-pyrimidin-6-one, followed by:

(i) reaction with metal alkoxide e.g. sodium, in the appropriate alcohol, such as methanol or ethanol, in pyridine solvent and in the presence of copper (I) iodide, preferably at a temperature from 80°–100° C., to give a compound of formula (III) where $R^7$ is alkoxy; or (ii) reaction with sodium hydride in a solvent, such as tetrahydrofuran, followed by alkyllithium e.g., tertiary-butyllithium, and subsequent reaction with a suitable electrophile, such as dimethylformamide or dialkyldisulphide, to give a compound of formula (III) where $R^7$ is formyl or $SR^{10}$.

The compound of formula (III) where $R^7$ is formyl can be further reacted with reducing agents, such as sodium borohydride or with Grignard reagents to give compounds of formula (III) where $R^7$ is 1-hydroxyalkyl.

Alternatively, compounds of formula (III) when $R^8$ is hydrogen can be prepared by reacting a compound of formula (XI):

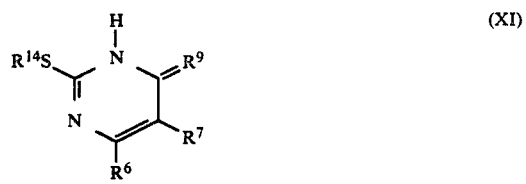

wherein $R^{14}$ is hydrogen or $C_1$–$C_4$ alkyl such as ethyl and $R^9$ is oxygen with Raney Nickel in an appropriate solvent such as aqueous ammonia.

Compounds of formula (XI) are either known compounds or they can be prepared from known compounds by known methods (see for example A Giner-Sorolla, A Bendick: J. Am. Chem. Soc., 1958, 80, 5744). Further details of the processes for preparation of the compounds may be ascertained from the Examples set out hereinafter.

The compounds of formula (I) may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of solid preparations that may be applied diluted or undiluted.

Solid compositions that may be applied undiluted may be in the form of dusting powders wherein the active ingredient is mixed with a solid diluent or carrier, e.g. kaolin, bentonite, kieselguhr, silica or talc. Or the solid composition may be in the form of granules wherein the active ingredient is absorbed on a non-porous granular material, for example, calcium carbonate, or may be impregnated in a porous granular material, for example, pumice or gypsum.

Solid compositions that may be applied diluted may be in the form of wettable powders wherein the active ingredient is mixed with a solid diluent or carrier, such as kaolin, kieselguhr or silica and appropriate surface acting agents or they may be in the form of water dispersible granules, wherein the active ingredient is mixed with a solid diluent or carrier, for example, kaolin, kieselguhr or silica and an appropriate surface acting agent, and then granulated.

Alternatively, the compositions may be in the form of liquid preparations to be used as dips, sprays or aerosol dispersions or non-aqueous solutions of the active ingredient and are usually diluted before application.

Aqueous dispersions of the active ingredient which may be applied diluted may be in the form of suspension concentrates wherein the active ingredient is dispersed in an aqueous media. These compositions contain dispersing/wetting agents and one or more stabilizing agents, for example, bentonite clays and/or polysaccharide gels. Additional further components may be included such as antifreeze agents, for example, ethylene glycol, propylene glycol or salts, and biocides, for example, Proxel GXL (1,2-benzisothiazolin-3-one).

Other aqueous dispersions of the active ingredient may be in the form of microcapsule suspensions wherein the active ingredient is encapsulated, as a high strength water immiscible solution, with a polymer and the subsequent microcapsules are dispersed in aqueous media. The microencapsulations technique used may be of the type described in the patent literature. These compositions contain dispersing/wetting agents and one or more stabilizing agents, for example, bentonite clays and/or polysaccharide gels. Additional further components may be included such as anti-freeze agents and biocides as previously described.

Other aqueous dispersions of the active ingredient may be in the form of oil in water emulsions wherein the active ingredient is dissolved in a suitable solvent, for example, an aromatic hydrocarbon such as trimethylbenzene or a ketonic solvent such as di-hydroisophorone alone with one or more emulsifying agents and then emulsifying the solution so obtained into water which may contain further surface active agents. Other suitable organic solvents are ethylene dichloride, toluene, kerosene, white oil, methylnapthalene, xylenes, trichloroethylene, vegetable oils, N-methyl-2-pyrrolidone and isophorone.

Alternatively liquid compositions may be in the form of non-aqueous solution to be used diluted or undiluted as sprays or aerosol fogs.

Non-aqueous preparations that may be applied undiluted may be in the form of low volume or ultra low volume concentrates wherein the active ingredient is dissolved in a suitable solvent or mixture of solvents, for example, an aromatic hydrocarbon such as trimethylbenzene or aliphatic hydrocarbon such as kerosene. Other suitable solvents are isophorone, di-hydroisophorone, toluene, xylenes, methylnapthalenes, N-methylpyrrolidone, mineral oil and vegetable oils. These preparations are optionally diluted before application with paraffinic solvents, such as diesel oil.

Other non-aqueous preparations may be in the form of emulsifiable concentrates wherein the active ingredient is dissolved in a suitable solvent, for example, trimethylbenzenes or methylcyclohexanone, with one or more emulsifying agents. Other suitable solvents are as previously described. These preparations are diluted in water to form aqueous dispersions before application.

Further formulation types may include preparations for special use such as aerosols wherein the composition will contain the active ingredient or ingredients, a propellant and an inert diluent, for example, odourless kerosenes or alkylated benzenes. In a preferred form, aerosol compositions may contain from 0.005% to 4% of active ingredient or ingredients, the remainder of the composition may be aqueous based in which an aqueous component is dispersed in a solution of active ingredient in a solvent, such as previously described, and a propellant by using one or more surface active agents. Aerosol compositions may optionally incorporate other additives, for example, knockdown agents, synergists, perfumes and corrosion inhibitors.

Other formulations for special purposes may be in the form of ready for use sprays wherein the active ingredient is dissolved in a solvent, for example, odourless kerosenes and alkylated benzenes and applied through a hard pump device to be used as a residual spray. These compositions may optionally incorporate other additives such as knockdown agents, synergists and perfumes.

Wetting agents, dispersing agents and emulsifying agents may be of the cationic, anionic or non-ionic type. Suitable agents of the cationic type include, for example, quaternary ammonium compounds, for example cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5–2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambacyhalothrin, biphenthrin, fenpropathrin, cyfluthrin, tefluthrin, fish safe pyrethroids for example etofenprox, natural pyrethrin, tetramethrin, s-bioallethrin, fenfluthrin, prallethrin and 5-benzyl-3-furylmethyl- (E)-(1R, 3S)-2,2-dimethyl-3-(2-oxothiolan-3-ylidenemethyl)-cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphosmethyl, fenitrothion or diazionon;

c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;

d) Benzoyl ureas such as triflumeron, or chlorofluazuron;

e) Organic tin compounds such as cyhexatin, fenbutatin oxide, azocyclotin;

f) Macrolides such as avermectins or milbemycins, for example, such as abamectin, avermectin, and milbemycin;

g) Hormones such as pheromones;

h) Organochlorine compounds such as benzene hexachloride, DDT, chlordane or dieldrin.

i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamax, and dodecyl imidazole.

Suitable herbicides, fungicides and plant growth regulators for inclusion in the compositions will depend upon the intended target and the effect required.

An example or a rice selective herbicide which can be included is propanil, an example of a plant growth regulator for use in cotton is "Pix", and examples of fungicides for use in rice include blasticides such as blasticide-S.

The ratio of the compound of the invention to the other active ingredient in the composition will depend upon a number of factors including type of target, effect required from the mixture, etc.

However, in general, the additional active ingredient of the composition will be applied at about the rate as it is usually employed, or at a slightly lower rate if synergism occurs.

The compositions of formula (I) and compositions comprising them have shown themselves active against a variety of insect and other invertebrate pests. They are particularly useful in controlling public health pests such as flies and cockroaches. They may also be active against organophosphate and pyrethroid resistant strains of pests such as houseflies (Musca domestica). They may be effective in combating both susceptible and resistant strains of the pests in their adult, larval and intermediate stages of growth, and may be applied to the infested host animal by topical, oral or parenteral administration.

The following Preparations and Examples illustrate various aspects of the invention. In the Preparations and Examples the compounds were identified and characterized by means of the melting points, nuclear magnetic resonance spectroscopy (in $CDCl_3$ or $d_6DMSO$, using a Jeol GSX machine at 270 mHz) or mass spectroscopy (using a VG TRIO 1).

PREPARATION 1

This description illustrates the preparation of 1-(4-amino-2,6-dichlorophenyl)-4-trifluoromethylpyrimidin-6-one.

1-(2,6-Dichloro-4-nitrophenyl)-4-trifluoromethylpyrimidin-6-one (2.0 g) was added in one portion to a stirred suspension of stannous chloride (4.46 g) in concentrated aqueous hydrochloric acid (50 ml) at ambient temperature. After a period of 6½ hours, the reaction mixture was poured into ice/water, made basic with aqueous sodium hydroxide solution, and extracted into ethyl acetate. The organic extracts were dried (magnesium sulphate), filtered, and evaporation of the solvent, under reduced pressure, gave 1-(4-amino-2,6-dichlorophenyl)-4-trifluoromethylpyrimidin-6-one as a yellow oil which solidified on standing (1.41 g). The compound showed:

Melting point: 156°–159° C.;
$^1$H NMR δ (CDCl$_3$): 8.03 (1H,s); 6.96 (1H,s); 6.75 (1H,s); 4.90 (2H, broad s).

PREPARATION 2

This description illustrates the preparation of 3,4,5-trichlorobenzonitrile.

A solution of 4-amino-3,5-dichloro-benzonitrile (5g) in dry acetonitrile (30ml) was added dropwise to a stirred suspension of copper (II) chloride (4.3 g) and t-butylnitrite (6.95 g) in dry acetonitrile (90 ml) while the reaction temperature was maintained between 0° and 5° C.

After the addition was complete, the reaction mixture was stirred for a further 1 hour at 5° C., and then allowed to warm slowly to the ambient temperature.

After a further two hours, the reaction mixture was poured into dilute aqueous hydrochloric acid and extracted into ethyl acetate. The combined organic extracts were washed with water and brine, dried over anhydrous magnesium sulphate, filtered and the solvent evaporated under reduced pressure to give an orange solid.

Recrystallisation from 1:1 mixture of ethyl acetate and petroleum ether (boiling range 60°–80° C.) gave 3,4,5-trichloro-benzonitrile.

$^1$H NMR δ (CDCl$_3$): 7.68 (s).

PREPARATION 3

This description illustrates the preparation of 4-fluoro-3,5-dichlorobenzonitrile.

A mixture of dry potassium fluoride (2.11 g), 18-Crown-6 (catalyst), and dry dimethylformamide (9 ml) in dry toluene (33 ml) was heated to reflux, and the distillate (35 ml) collected. The residue was cooled and 3,4,5-trichlorobenzonitrile (3.76 g) was added. This solution was stirred and heated to 140° C. for 4 days. On cooling to ambient temperature, the reaction mixture was filtered and the residue washed with ethyl acetate. The combined filtrates were washed with water, dried over anhydrous magnesium sulphate and filtered. Evaporation of the solvent under reduced pressure gave a brown solid composed of a 2:1 mixture of 3,4,5-trichlorobenzonitrile and 4-fluoro-3,5-dichloro- benzonitrile which was used without further purification.

$^1$H NMR δ (CDCl$_3$): 7.69 (4/3H,s); 7.67 (2/3H,d).

PREPARATION 4

This description illustrates the preparation of 6-nitro-2,4-bis-(trifluoromethyl)-bromobenzene.

Concentrated nitric acid (2.6 ml) was cautiously added to a solution of 2,4-bis(trifluoromethyl)bromobenzene (16 g) in concentrated sulphuric acid (48 ml), and the mixture was heated to 80° C. for 6 hours. After cooling to ambient temperature and allowing to stand overnight, the reaction mixture was cautiously poured onto ice, and extracted with ethyl acetate. The organic extracts were washed with water and brine and dried over magnesium sulphate. Evaporation of the solvent, under reduced pressure, gave 6-nitro-2,4-bis(trifluoromethyl) bromobenzene as a yellow liquid.

$^1$H NMR δ (CDCl$_3$): 8.12 (1H,s); 8.08 (1H,s).

The NMR spectrum showed the material to be contaminated with a small amount of residual 2,4-bis(trifluoromethyl) bromobenzene, which was removed at the next stage.

PREPARATION 5

This description illustrates the preparation of 1-(2-amino-4,6-bis-(trifluoromethyl)-4-trifluoromethyl pyrimidin-6-one.

Reduced iron powder (0.21 g) was added to a suspension of 1-(2-nitro-4,6-bis-(trifluoromethyl)-4-trifluoromethyl pyrimidin-6-one (Compound No. 2 in Table I) (1.5 g) in a mixture of isopropanol (12 ml) and water (2 ml).

Concentrated hydrochloric acid (1 drop) was added, and after standing for 16 hours, the reaction mixture was heated to 80° C. for a total of 10 hours. After cooling to the ambient temperature, and allowing to stand for 2 days, the reaction mixture was filtered through celite and the residue washed with ethyl acetate. Evaporation of the filtrate under reduced pressure gave a viscous brown oil. The oil was chromatographed on a column of silica gel using petroleum ether (boiling range 60°–80° C.) containing ethyl acetate (30% by volume) as eluent. The appropriate fractions were further chromatographed using petroleum ether (boiling range 60°–80° C.) containing diethyl ether (20% by volume) as eluent, followed by ethyl acetate, to give 1-(2-amino-4,6-bis-(trifluoromethyl)-4-trifluoromethyl pyrimidin-6-one.

$^1$H NMR δ (CDCl$_3$): 8.05 (1H,s); 7.45 (1H,s); 7.38 (1H,s); 7.00 (1H,s); 4.15 (2H,s).

PREPARATION 6

This description illustrates the preparation of 2-chloro-4-trifluoromethoxy-6-nitro-aniline.

Chlorine gas was passed through a solution of 2-nitro-4-trifluoromethoxy-aniline (14.5 g) in carbon tetrachloride (175 ml). As the mixture was stirred it became solid and more carbon tetrachloride (50 ml) was added. Chlorine gas was passed through the reaction mixture until thin layer chromatography (silica gel, using petroleum ether (boiling range 60°–80° C.) containing ethyl acetate (30% by volume) as eluent) demonstrated the absence of starting material. Evaporation of the solvent under reduced pressure gave a dark orange solid, which on trituration with petroleum ether (boiling range 60°–80° C.) gave a 2-chloro-4-trifluoromethoxy-6-nitro-aniline as an orange solid.

$^1$H NMR δ (CDCl$_3$): 8.04 (1H,d); 7.49 (1H,d); 6.60 (2H,br.s)

PREPARATION 7

3,4-Dichloro-5-nitro-trifluoromethoxy-benzene was prepared from 2-chloro-4-trifluoromethoxy-6-nitro-aniline according to the procedure given in Preparation 2. Kugelrohr distillation under reduced pressure (0.25 mm Hg, 80° C.) gave the desired product.

$^1$H NMR δ (CDCl$_3$): 7.60 (fine d).

PREPARATION 8

3-chloro-4-fluoro-5-nitro-trifluoromethoxybenzene was prepared from 3,4-dichloro-5-nitro-trifluoromethoxy benzene according to the procedure given in Preparation 3. Kugelrohr distillation under reduced pressure (15 mmHg, 125° C.) gave the desired product (contaminated with starting material). This material was used without further purification.

electron impact, m/e: 259/261 (M+).

PREPARATION 9

1-(2-Amino-6-chloro-4-trifluoromethoxyphenyl)-4-trifluoromethylpyrimidin-6-one was prepared from 1-(2-chloro-6-nitro-4-trifluoromethoxyphenyl)-4-trifluoromethylpyrimidin-6-one (Compound No. 13 in Table I) according to the procedure given in Preparation 5.

$^1$H NMR $\delta$ (CDCl$_3$): 8.04 (1H,s); 7.00 (1H,s); 6.85 (1H,fine d); 6.66 (1H,fine d); 4.00 (2H,broad s)

PREPARATION 10

1-(2-amino-6-chloro-4-trifluoromethoxyphenyl)-4-penta fluoroethylpyrimidin-6-one was prepared from 1-(2-chloro-6-nitro-4-trifluoromethoxyphenyl)-4-pentafluoroethylpyrimidin-6-one (Compound No. 17 in Table I) according to the procedure given in Preparation 5.

$^1$H NMR $\delta$ (CDCl$_3$): 8.02 (1H,s); 7.02 (1H,s); 6.79 (1H,d); 6.69 (1H,d); 4.6 (2H,broad s)

PREPARATION 11

This description illustrates the preparation of 3,5-dichloro-4-fluoro-nitrobenzene.

A solution of 3,4,5-trichloro-nitrobenzene (30.0 g) and anhydrous potassium fluoride (11.5 g) in dry dimethylformamide (60 ml) was heated to 140° C. for a period of 20 hours. After cooling to the ambient temperature, the reaction mixture was poured into water and extracted with diethyl ether. The combined ether layers were washed with water and brine and dried. Evaporation of the solvent under reduced pressure gave a brown oil. This crude product was passed through a plug of silica using hexane containing ethyl acetate (15% by volume) as eluent to give 2,4-dichloro-3-fluoro-nitrobenzene as an orange solid.

$^1$H NMR $\delta$ (CDCl$_3$): 8.26 (d).

PREPARATION 12

3,5-Dichloro-4-fluoro-aniline was prepared from 3,5-dichloro-4-fluoro-nitrobenzene according to the method given in Preparation 1.

$^1$H NMR $\delta$ (CDCl$_3$): 6.59 (2H,d); 3.64 (2H,broad s)

PREPARATION 13

3,5-Dichloro-4-fluoro-iodobenzene was prepared from 3,5-dichloro-4-fluoro-aniline according to the procedure given in Preparation 2. In this preparation the halide used was copper (I) iodide and purification of the product was achieved by passing the crude product through a plug of silica gel using hexane as eluent.

$^1$H NMR $\delta$ (CDCl$_3$): 7.63 (d)

PREPARATION 14

This description illustrates the preparation of 3,5-dichloro-4-fluoro-pentafluoroethylbenzene.

A mixture of 3,5-dichloro-4-fluoro-iodobenzene (10 g), copper (I) iodide (13.4 g), and anhydrous sodium pentafluoropropionate (24.6 g) in dry dimethylformamide (200 ml) was heated to 130° C. for a period of 21 hours. After cooling to the ambient temperature, the reaction mixture was diluted with diethyl ether and filtered through a plug of celite. The filtrate was washed with water, dried, and the solvent removed by distillation at atmospheric pressure. Distillation of the brown oily residue under reduced pressure gave several fractions, boiling range 72°–76° C., 80°–82° C., 90°–96° C. and 90° C. (84 mmHg), all of which contained 3,5-dichloro-4-fluoropentafluoroethylbenzene as the major component.

$^1$H NMR $\delta$ (CDCl$_3$): 7.56 (d)

$^{19}$F NMR $\delta$ (CDCl$_3$): −85.04 (3F); −109.4 (1F); −115 (2F)

PREPARATION 15

This description illustrates the preparation of N-(2,6-dichloro-4-trifluoromethylphenyl)-thiourea. A solution of sodium thiocyanate (16 g) and benzoyl chloride (24 g) in acetone (180 ml) was heated to reflux. A solution of 2,6-dichloro-4-trifluoromethyl aniline (20 g) in acetone (70 ml) was then added dropwise whilst the reaction mixture was maintained at reflux. After the addition was complete, heating was continued for a further six hours, whereupon the reaction mixture was allowed to cool to the ambient temperature, and poured into water. The precipitate was collected, washed with water and dried. The filtrate was extracted with ethyl acetate. Evaporation of the solvent, under reduced pressure, gave a yellow solid, which was added to the earlier collected residue. The combined solids were added to a 10% aqueous sodium hydroxide solution, and heated to 60° C. for 16 hours. The reaction mixture was then acidified (while hot) with concentrated hydrochloric acid (with care) and finally basified with aqueous ammonium hydroxide solution. The precipitate was collected, and recrystallised from a mixture of ethyl acetate and petroleum ether (boiling range 60°–80° C.) to give the desired compound as fine white needles.

melting point: 165°–166.2° C.

$^1$H NMR $\delta$ (CDCl$_3$): 8.73 (1H,broad s); 7.65 (2H,s); 6.50 (2H,broad s)

PREPARATION 16

This description illustrates the preparation of S-methyl-N-(2,6-dichloro-4-trifluoromethylphenyl)isothiourea.

Sodium hydride (60% dispersion in oil) (0.98 g) was added to a solution of N-(2,6-dichloro-4-trifluoromethyl phenyl)-thiourea (6.45 g)(Preparation 15) in dry dimethyl formamide (45 ml). After stirring at the ambient temperature for 30 minutes, methyl iodide (6.33 g) was added in one portion, and the reaction mixture was stirred at room temperature for a period of 16 hours. The reaction mixture was then poured into water and extracted with ethyl acetate. The combined organic extracts were washed with water and dried. Evaporation of the solvent under reduced pressure gave a brown oil. This residue was passed through a plug of silica using petroleum ether (boiling range 60°–80° C.) containing ethyl acetate (33% by volume) as eluent to give the desired compound as a pale yellow oil.

$^1$H NMR $\delta$ (CDCl$_3$): 7.50 (2H,s); 4.62 (2H,broad s); 2.46 (3H,s)

PREPARATION 17

This description illustrates the preparation of N-(2,6-dichloro-4-trifluoromethylphenyl)-3-amino-4,4,4-tri fluorobut-2-en-1-amide.

A solution of 1-(2,6-dichloro-4-trifluoromethyl phenyl)-4-trifluoromethylpyrimidin-6-one (2.5 g) (EP 0338686) and diethylamine (40 ml) in methanol (40 ml) was heated to reflux for a period of 48 hours. After cooling to the ambient temperature, evaporation of the solvent, and excess diethylamine, under reduced pressure, gave a yellow oil. Chromatography on silica gel using dichloromethane as eluent gave the desired compound as a white solid.

melting point: 147°-150° C.

$^1$H NMR δ (CDCl$_3$): 7.66 (2H,s); 6.88 (1H,broad s); 6.50 (2H,broad); 5.20 (1H,s)

PREPARATION 18

This description illustrates the preparation of 5-methylthio-4-trifluoromethylpyrimidin-6-one.

Sodium hydride (0.99 g of 55% oil dispersion) was washed with hexane, suspended in dry tetrahydrofuran (100 ml) and stirred under nitrogen. To this was added 5-bromo-4-trifluoromethylpyrimidin-6-one (EP 0338686) (5.00 g) in portions over 5 minutes. The resulting solution was stirred for 20 minutes then cooled to −78° C. and tertiary butyl lithium (26.6 ml of 1.7M solution in pentane) was added dropwise over 1 hour. After a further 10 minutes stirring at −78° C., dimethyl disulphide (9.3 ml) was added in one portion. The mixture was stirred at −78° C. for 5 hours, allowed to warm to room temperature slowly and allowed to stand for two days. The mixture was then quenched with 2M HCl and extracted with ethyl acetate. The extracts were dried over magnesium sulphate and concentrated by evaporation of the solvent under reduced pressure to give 4.6 g of pale yellow solid. Recrystallisation from chloroform/hexane gave an off-white solid.

melting point: 182.3°-184.5° C.

$^1$H NMR δ (d$_6$—DMSO): 8.30 (1H,s); 2.35 (3H,s).

PREPARATION 19

This description illustrates the preparation of 5-formyl-4-trifluoromethylpyrimidin-6-one.

Sodium hydride (0.99 g of 55% oil dispersion) was washed with hexane and suspended in dry tetrahydrofuran under nitrogen. With stirring, 5-bromo-4-trifluoromethylpyrimidin-6-one (5.0 g) was added in portions over 5 minutes. The mixture was stirred at room temperature for 30 minutes and then cooled to −78° C. Tertiary butyl lithium (26.6 ml of 1.7M solution in pentane) was added dropwise over 30 minutes keeping the temperature below −78° C. The mixture was stirred for a further 2 hours at −78° C. then anhydrous dimethylformamide (6.4 ml) was added over 1 minute. The mixture was allowed to warm to room temperature over 5 hours, quenched with 2M hydrochloric acid and extracted with ethyl acetate. The extracts were dried over magnesium sulphate and concentrated by evaporation of the solvent under reduced pressure. Recrystallisation of the residue from toluene gave 2.0 g of a pale yellow solid.

melting point: 141.1°-143.5° C.

$^1$H NMR δ (d$_6$DMSO): 13.8 (1H,s); 10.1 (1H,s); 8.50 (1H,s)

PREPARATION 20

This description illustrates the preparation of 5-ethoxy-4-trifluoromethylpyrimidin-6-one.

Pyridine (30 ml) was added to a solution of sodium metal (0.76 g) in ethanol (20 ml) followed by 5-bromo-4-trifluoromethylpyrimidin-6-one (2.0 g) and cuprous iodide (1.6 g). The mixture was stirred under nitrogen at room temperature for ½ hour and then heated at 100° C. for 5¼ hours. The mixture was cooled and 2M hydrochloric acid was added and the mixture extracted with ethyl acetate. The extracts were washed with brine, dried over magnesium sulphate and concentrated by evaporation of the solvent under reduced pressure. The brown residue was dissolved in ethyl acetate, treated with charcoal and filtered, then the filtrate concentrated by evaporation of the solvent under reduced pressure and the residue recrystallised from toluene to give 883 mg of a buff solid. A further 580 mg of a pale yellow solid were obtained by concentrating the mother liquors and subliming the residue at 150° C./1 mm.

melting point: 134.8°-137.0° C.

$^1$H NMR δ (d$_6$-DMSO): 8.00 (1H,s); 4.20 (2H,q,); 1.20 (3H,t); 13.2 (1H,br s)

PREPARATION 21

This description illustrates the preparation of 5-methyl-4-trifluoromethylpyrimidin-6-one.

Raney nickel (3.45 g of 50% dispersion in water) was added to a suspension of 5-methyl-6-trifluoromethyl-2-thiouracil (prepared according to Preparation 22) (2.0 g) in water (25 ml) containing ammonia (0.96 ml of 0.88d solution) and the mixture was refluxed for 4½ hours. The mixture was filtered hot and the residue washed with hot methanol. The combined filtrates were concentrated by evaporation of the solvent under reduced pressure to a pale green solid. Sublimation (130° C./0.07 mm) gave 0.98 g of a very pale green solid.

melting point: 174.9°-176.4° C.

$^1$H NMR δ (CDCl$_3$): 8.15 (1H,s); 2.25 (3H,s)

PREPARATION 22

This description illustrates the preparation of 5-methyl-6-trifluoromethyl-2-thiouracil.

Sodium metal (3.34 g) was dissolved in methanol (61.5 ml), then thiourea (14.36 g) and ethyl 4,4,4-trifluoro-2-methylacetoacetate (25 g) were added. The mixture was refluxed for 47½ hours and concentrated by evaporation of the solvent under reduced pressure to give a brown solid. The solid was dissolved in water, then the solution was acidified with hydrochloric acid and extracted with ether. The extracts were dried over magnesium sulphate and concentrated by evaporation of the solvent under reduced pressure. Stirring the residue with hexane/ether and filtering gave 7.3 g of a light brown solid.

melting point: 233.0°-234.6° C.

$^1$H NMR δ (d$_6$-DMSO): 1.9 (3H,s); 12.8 (2H, broad s)

PREPARATION 23

This description illustrates the preparation of 5-hydroxymethyl-4-trifluoromethylpyrimidin-6-one.

5-Formyl-4-trifluoromethylpyrimidin-6-one (0.5 g) (as prepared in Preparation 19) was added in portions over 10 minutes to a stirred suspension of sodium borohydride (0.1 g) in ethanol (10 ml). After 2 hours the solution was concentrated and 2M HCl added to the residue. The mixture was extracted with ethyl acetate and the extracts washed with brine, dried over magnesium sulphate and concentrated to an off white solid (0.353 g).

melting point; 186°-188.8° C.

$^1$H NMR δ (d$_6$-DMSO): 13.15 (1H,broad s); 8.25 (1H,s); 4.35 (2H,s)

PREPARATION 24

This description illustrates the preparation of 5-(1-hydroxyethyl)-4-trifluoromethylpyrimidin-6-one.

Methyl magnesium bromide (1.82 ml of 3M solution in ether) was added over 20 minutes to a solution of 5-formyl-4-trifluoromethylpyrimidin-6-one (0.5 g) (as prepared in Preparation 19) in dry tetrahydrofuran (15 ml) keeping the temperature below 5° C. The mixture was allowed to warm to room temperature and stirred for 3 hours. The mixture was quenched with 2M HCl and extracted with ethyl acetate. The extracts were washed with brine, dried over magnesium sulphate and concentrated by evaporation of the solvent under reduced pressure to give a buff solid. The solid product (0.423 g) was obtained by recrystallisation from ethyl acetate/hexane.

melting point: 145°–146.6° C.

$^1$H NMR δ (d$_6$-DMSO): 13.2 (1H,broad s); 8.25 (1H,s); 5.0 (1H,m); 4.8 (1H,d); 1.35 (3H,d)

EXAMPLE 1

This Example illustrates the preparation of 1-(2,6-dichloro-5-methyl-4-trifluoromethylphenyl)-4-trifluoromethylpyrimidin-6-one (Compound No. 1 in Table I).

A dry reaction flask was purged with nitrogen and charged with a 50% suspension of sodium hydride (0.24 g). The sodium hydride was washed with pentane and suspended in dry dimethylformamide (DMF, 10 ml).

6-Trifluoromethylpyrimidin-6-one (0.75 g) was added portionwise, and when the addition was complete the reaction was stirred for a further 30 minutes. 3,5-Dichloro-4-fluoro-2-methyl-trifluoromethylbenzene (2.26 g) (EP 0259048) was added and the reaction mixture was heated to 90° for 16 hours. The reaction was allowed to cool, poured into water and extracted with ethyl acetate. The organic layer was washed with brine, dried over magnesium sulphate and evaporated under reduced pressure to give a pale brown solid. The solid was flushed through a silica plug using diethyl ether (20% by volume) in petroleum ether (boiling range 60°–80°) as eluent. Evaporation of the solvent, under reduced pressure, gave a pale brown solid which was triturated with petrol, and recrystallised from petroleum ether (boiling range 60°–80°) containing a small amount of ethyl acetate, to give 1-(2,6-dichloro-5-methyl-4-trifluoromethylphenyl)-4-trifluoromethylpyrimidin-6-one as white needles:

melting point: 204°–205.5° C.

$^1$H NMR δ (CDCl$_3$): 8.00 (1H, s), 7.83 (1H, s), 7.0 (1H, s) 2.58 (3H, s)

EXAMPLE 2

The following compounds were prepared according to the general method of Example 1.

a) 1-(2,4-Bis-(trifluoromethyl)-6-nitrophenyl)-4-trifluoromethylpyrimidin-6-one (Compound No. 2 in Table I); from 6-nitro-2,4-bis-(trifluoromethyl)-bromobenzene (as prepared in Preparation 4).

melting point: 142°–143° C.

$^1$H NMR δ (CDCl$_3$): 8.70 (1H, s); 8.45 (1H, s); 8.14 (1H, s); 6.95 (1H, s)

$^{19}$F NMR δ (CDCl$_3$): −60.38 (3F, s); −63.76 (3F, s); −72.11 (3F, s).

b) 1-(2,6-Dichloro-4-nitrophenyl)-4-trifluoromethyl-pyrimidin-6-one (Compound No. 5 in Table I) from 3,5-dichloro-4-fluoro-nitrobenzene (as prepared in Preparation 11).

melting point: 138°–139.8° C.

$^1$H NMR δ (CDCl$_3$): 8.41 (2H, s); 8.00 (1H, s); 7.00 (1H, s)

c) 1-(2,4-Bis-(trifluoromethyl)-6-nitrophenyl)-5-bromo-4-trifluoromethylpyrimidin-6-one (Compound No. 8 in Table I) from 6-nitro-2,4-bis(trifluoromethyl)-bromobenzene (as prepared in Preparation 4) and 5-bromo-4-trifluoromethyl-pyrimidin-6-one.

melting point: 135.5°–137° C.

$^1$H NMR δ (CDCl$_3$): 8.75 (1H,s); 8.45 (1H,s); 8.05 (1H,s)

d) 1-(2-Chloro-6-nitro-4-trifluoromethoxyphenyl)-4-trifluoromethylpyrimidin-6-one (Compound No. 13 in Table I) from 3,4-dichloro-5-nitro-(trifluoromethoxy) benzene (as prepared in Preparation 7), on heating at 90° C. for 16 hours. The compound required extensive purification on a Gilson medium performance liquid chromatography column using silica gel and eluting with hexane containing ethyl acetate (5% by volume) followed by recrystallisation from petroleum ether (boiling range 60°–80° C.) containing ethyl acetate (16% by volume).

$^1$H NMR δ (CDCl$_3$): 8.1 (1H,s); 8.05 (1H,d); 7.80 (1H,d); 6.98 (1H,s)

e) 1-(2-Chloro-6-nitro-4-trifluoromethoxyphenyl)-4-pentafluoroethylpyrimidin-6-one (Compound No. 17 in Table I) from 3,4-dichloro-5-nitro-(trifluoromethoxy) benzene (as prepared in Preparation 7) and 4-pentafluoroethyl-pyrimidin-6-one, on heating at 90° C. for 16 hours. The compound required purification on a Gilson medium performance liquid chromatography column using silica gel and eluting with hexane containing ethyl acetate (5% by volume).

melting point: 139°–140.5° C.

$^1$H NMR δ (CDCl$_3$): 8.10 (1H,s); 8.05 (1H,d); 7.80 (1H,d); 7.00 (1H,s)

In an alternative procedure 1-(2-chloro-6-nitro-4-trifluoromethoxyphenyl)-4-pentafluoroethyl pyrimidin-6-one was prepared from 3-chloro-4-fluoro-5-nitro-(trifluoromethoxy)benzene (the product of Preparation 8) by stirring at ambient temperature.

f) 1-(2,6-Dichloro-4-pentafluoroethylphenyl)-4-trifluoromethylpyrimidin-6-one (Compound No. 19 in Table I) from 3,5-dichloro-4-fluoro-pentafluoromethyl benzene (as prepared in Preparation 14).

melting point: 122°–125° C.

$^1$H NMR δ (CDCl$_3$): 8.01 (1H,s); 7.78 (2H,s); 7.01 (1H,s)

g) 1-(2,6-dichloro-4-(pentafluoroethyl)-phenyl)-4-pentafluoroethylpyrimidin-6-one (Compound No. 20 in Table I), from 3,5-dichloro-4-fluoropentafluoroethyl benzene.

melting point: 165°–167° C.

$^1$H NMR δ (CDCl$_3$): 8.0 (1H,s); 7.79 (2H,s); 7.05 (1H,s)

EXAMPLE 3

This Example illustrates the preparation of 1-(2,4,6-trichlorophenyl)-4-trifluoromethylpyrimidin-6-one (Compound No. 3 in Table I).

A solution of 1-(4-amino-2,6-dichlorophenyl)-4-trifluoromethylpyrimidin-6-one (as prepared in Preparation 1) (0.9 g) in acetonitrile (10 ml) was added dropwise to a stirred suspension of copper (II) chloride (0.37 g) and t-butylnitrite (1.46 g) in dry acetonitrile (8 ml) while the temperature was maintained between 0° and 5° C. After the addition was complete, the reaction mixture was stirred for a further 1 hour at 5° C., and then allowed to warm slowly to ambient temperature. The reaction mixture was then poured into 20% aqueous hydrochloric acid and extracted into diethyl ether. The combined organic extracts were washed with 20% aqueous hydrochloric acid, dried over anhydrous magnesium sulphate, filtered, and the solvent evaporated under reduced pressure. The residual oil was flushed through a plug of silica gel using petroleum ether (boiling range 60°–80° C.) containing diethyl ether (25% by volume) as eluent. Recrystallisation of the so generated white solid from petroleum ether (boiling range 60°–80° C.) gave 1-(2,4,6-trichlorophenyl)-4-trifluoromethylpyrimidin-6-one.

melting point 154.5°–156.5° C.;

$^1$H NMR δ (CDCl$_3$): 7.98 (1H,s); 7.57 (2H,s); 6.98 (1H,s)

EXAMPLE 4

The following compounds were prepared according to the general method of Example 3.

a) 1-(2,6-Dichloro-4-iodophenyl)-4-trifluoromethylpyrimidin-6-one (Compound No. 4 in Table I) from 1-(4-amino-2,6-dichlorophenyl)-4-trifluoromethylpyrimidin-6-one (as prepared in Preparation 1). In this Example copper (I) iodide was the halide used, and the organic extract was washed with aqueous sodium metabisulphite solution before further work-up. The compound showed:

melting point: 148°–149.3° C.

$^1$H NMR δ (CDCl$_3$): 7.99 (1H,s); 7.90 (2H,s); 6.98 (1H,s)

b) 1-(4-Bromo-2,6-dichlorophenyl)-4-trifluoromethylpyrimidin-6-one (Compound No. 6 in Table I) from 1-(4-amino-2,6-dichlorophenyl)-4-trifluoromethyl pyrimidin-6-one (as prepared in Preparation 1). In this Example copper (II) bromide was the halide used.

melting point: 150°–155° C.

$^1$H NMR δ (CDCl$_3$): 7.98 (1H,s); 7.72 (2H,s); 6.9 (1H,s)

c) 1-(2-Chloro-4,6-bis-(trifluoromethyl)-phenyl)-4-trifluoromethylpyrimidine-6-one (Compound No. 9 in Table I) from 1-(2-amino-4,6-bis-(trifluoromethyl)phenyl-4-trifluoromethylpyrimidin-6-one (as prepared in Preparation 5). In this Example, copper (II) chloride was the halide used.

melting point: 133.5°–135.5° C.

$^1$H NMR δ (CDCl$_3$): 8.15 (1H,s); 8.05 (1H,s); 8.00 (1H,s); 6.95 (1H,s)

d) 1-(2-Bromo-4,6-bis-(trifluoromethyl)-phenyl)-4-trifluoromethylpyrimidin-6-one (Compound No. 11 in Table I) from 1-(4-amino-4,6-bis-(trifluoromethyl)phenyl-4-trifluoromethylpyrimidin-6-one (the product of preparation 5). In this Example copper (II) bromide was the halide used.

melting point: 134°–138° C.

$^1$H NMR δ (CDCl$_3$): 8.30 (1H,s); 8.10 (1H,s); 7.98 (1H,s); 6.99 (1H,s)

e) 1-(2,6-Dichloro-4-trifluoromethoxyphenyl)-4-trifluoromethylpyrimidine-6 -one (Compound No. 14 in Table I from 1-(2-amino-6-chloro-4-trifluoromethoxyphenyl)-4-trifluoromethylpyrimidin-6-one (the product of Preparation 9). In this Example copper (II) chloride was the halide used.

melting point: 130.5°–132.5° C.

$^1$H NMR δ (CDCl$_3$): 8.00 (1H,s); 7.44 (2H,s); 7.00 (1H,s)

f) 1-(2-Bromo-6-chloro-4-trifluoromethoxyphenyl)-4-trifluoromethylpyrimidin-6-one (Compound No. 15 in Table I) from 1-(2-amino-6-chloro-4-trifluoromethoxyphenyl)-4-trifluoromethylpyrimidin-6-one (the product of Preparation 9). In this Example copper (II) bromide was the halide used.

melting point: 128°–131° C.

$^1$H NMR δ (CDCl$_3$): 8.00 (1H,s); 7.60 (1H,d); 7.49 (1H,d); 6.99 (1H,s)

g) 1-(2,6-Dichloro-4-trifluoromethoxyphenyl)-4-pentafluoroethylpyrimidin-6-one (Compound No. 18 in Table I) from 1-(2-amino-6-chloro-4-trifluoromethoxyphenyl)-4-pentafluoroethylpyrimidin-6-one (the product of Preparation 10). In this Example copper (II) chloride was the halide used.

melting point: 168°–169° C.

$^1$H NMR δ (CDCl$_3$): 8.00 (1H,s); 7.45 (2H,s); 7.03 (1H,s)

h) 1-(2,6-Dichloro-4-methylthiophenyl)-4-trifluoromethyl pyrimidin-6-one (Compound No. 44·of Table 1), from 1-(4-amino-2,6-dichlorophenyl)-4-trifluoromethyl pyrimidinone (the product of Preparation 1). In this example the copper salts were replaced with dimethyl disulphide (1.2 equivalents).

melting point: 108°–111° C.

$^1$H NMR δ (CDCl$_3$): 8.00 (1H,s); 7.33 (2H,broad s), 6.98 (1H,s); 2.55 (3H,s)

i) 1-(2-Bromo-6-chloro-4-trifluoromethoxyphenyl)-4-pentafluoroethylpyrimidin-6-one (Compound No. 49 in Table I) was prepared from 1-(2-amino-6-chloro-4-trifluoromethoxyphenyl)-4-pentafluoroethylpyrimidin-6-one (the product of Preparation 10). In this preparation copper II bromide was the halide used.

$^1$H NMR δ (CDCl$_3$): 8.00 (1H,s); 7.60 (1H,d); 7.50 (1H,d); 7.05 (1H,s)

EXAMPLE 5

This Example illustrates the preparation of 1-(2-chloro-6-methoxy-4-trifluoromethylphenyl)-4-trifluoromethyl-pyrimidin-6-one (Compound No. 7 in Table I).

1-(2-Chloro-6-fluoro-4-trifluoromethylphenyl)-4-trifluoromethylpyrimidin-6-one (0.5 g) (EP 0338686) was added to a solution of sodium methoxide, prepared by reacting sodium metal (0.03 g) with dry methanol (10 ml). After stirring at ambient temperature for 24 hours, evaporation of the solvent under reduced pressure gave a viscous oil which crystallised on standing. This material was subjected to column chromatography on silica gel using petroleum ether (boiling range 60°–80° C.) containing ethyl acetate (30% by volume) as eluent. The earlier fractions were collected, and after evaporation of the solvent under reduced pressure and then trituration with boiling petroleum ether (boiling range 60°–80° C.), gave the desired compound as a white solid.

$^1$H NMR δ (CDCl$_3$): 7.98 (1H,s); 7.49 (1H,s); 7.22 (1H,s); 6.98 (1H,s); 3.93 (3H,s)

EXAMPLE 6

This Example illustrates the preparation of 1-(2-chloro-4,6-bis-(trifluoromethyl)-phenyl)-5-bromo-4-trifluoromethylpyrimidin-6-one (Compound No. 10 in Table I).

Liquid bromine (0.086 g) was added to a stirred solution of 1-(2-chloro-4,6-bis-(trifluoromethyl)-phenyl)-4-trifluoromethylpyrimidin-6-one (i.e. Compound No. 9 in Table I) (0.2 g) and sodium acetate trihydrate (0.2 g) in acetic acid (3 ml). The stoppered flask was stirred at ambient temperature for 16 hours. Evaporation of the solvent under reduced pressure gave a yellow solid which was dissolved in ethyl acetate and washed consecutively with water, aqueous sodium thiosulphate solution, and brine. After drying, evaporation of the solvent under reduced pressure gave a yellow solid.

Flushing this material through a plug of silica gel using petroleum ether (boiling range 60°–80° C.) containing diethyl ether (20% by volume) as eluent, gave the desired compound as a pale yellow solid.

melting point: 136°–139° C.

$^1$H NMR δ (CDCl$_3$): 8.15 (1H,s); 8.05 (1H,s); 7.92 (1H, s).

EXAMPLE 7

The following compounds were prepared according to the general method of Example 6.

(a) 1-(2-Bromo-4,6-bis-(trifluoromethyl)-phenyl)-5-bromo-4-trifluoromethylpyrimidin-6-one (Compound No. 12 in Table I) from 1-(2-bromo-4,6-bis-(trifluoromethyl)phenyl-4-trifluoromethylpyrimidin-6-one (Compound No. 11 in Table I).

$^1$H NMR δ (CDCl$_3$): 8.30 (1H,s); 8.10 (1H,s); 7.95 (1H,s)

(b) 1-(2,6-Dichloro-4-trifluoromethoxyphenyl)-5-bromo-4-trifluoromethylpyrimidin-6-one (Compound No. 16 in Table I) from 1-(2,6-dichloro-4-trifluoromethoxyphenyl)-4-trifluoromethylpyrimidin-6-one (Compound No. 15 in Table I).

melting point: 130°–132° C.

$^1$H NMR δ (CDCl$_3$): 7.95 (1H,s); 7.45 (2H,s)

(c) 1-(2,6-Dichloro-4-pentafluoroethylphenyl)-5-bromo-4-trifluoromethylpyrimidin-6-one (Compound No. 21 in Table I) from 1-(2,6-dichloro-4-(pentafluoroethyl)phenyl)-4-trifluoromethyl-pyrimidin-6-one (Compound No. 19 in Table I).

melting point: 137°–140° C. (decomposition)

$^1$H NMR δ (CDCl$_3$): 7.97 (1H,s); 7.79 (2H,s)

(d) 1-(2,6-Dichloro-4-pentafluoroethylphenyl)-5-bromo-4-pentafluoroethylpyrimidin-6-one (Compound No. 22 in Table I) from 1-(2,6-dichloro-4-pentafluoroethyl phenyl-4-pentafluoroethyl-pyrimidin-6-one (Compound No. 20 in Table I).

melting point: 130° C. (decomposition)

$^1$H NMR δ (CDCl$_3$): 7.94 (1H,s); 7.80 (2H,s)

EXAMPLE 8

This Example illustrates the preparation of 1-(2,6-dichloro-4-trifluoromethylphenyl)-2-methylthio-4-trifluoromethylpyrimidin-6-one (Compound No. 23 in Table I).

A solution of S-methyl-N-(2,6-dichloro-4-trifluoromethylphenyl)isothiourea (1.0 g) (as prepared in Preparation 16) in dry tetrahydrofuran (4 ml) was added dropwise to a stirred suspension of sodium hydride (0.16 g) in dry tetrahydrofuran (7 ml). Hydrogen was evolved over the period of one hour, whereupon a solution of methyl-4,4,4-trifluorobutynoate (0.75 g) in tetrahydrofuran (1 ml) was added dropwise. Stirring was continued at ambient temperature for a period of 16 hours, at which point the reaction mixture was poured into water, acidified with dilute hydrochloric acid and extracted with ethyl acetate. The combined organic extracts were dried over magnesium sulphate, filtered and the solvent evaporated under reduced pressure to give an orange gum. Column chromatography on silica using petroleum ether (boiling range 60°–80° C.) containing ethyl acetate (8% by volume) as eluent, followed by trituration with petroleum ether (boiling range 60°–80° C.) gave the desired compound as as fine white needles.

melting point: 156°–157.6° C.

$^1$H NMR δ (CDCl$_3$): 7.79 (2H,s); 6.69 (1H,s); 2.59 (3H,s)

EXAMPLE 9

This Example illustrates the preparation of 1-(2,6-dichloro-4-trifluoromethylphenyl)-2-methylsulphinyl-4-trifluoromethylpyrimidin-6-one (Compound No. 24 in Table I).

m-Chloroperbenzoic acid (0.33 g) was added to a stirred solution of 1-(2,6-dichloro-4-trifluoromethyl phenyl)-2-methylthio-4-trifluoromethylpyrimidin-6-one (the product of Example 8) (0.20 g) in chloroform (6 ml). After stirring for a period of 30 minutes, the reaction mixture was diluted with chloroform and washed sequentially with aqueous sodium bicarbonate solution, aqueous sodium bisulphite solution, and finally brine. After drying over anhydrous magnesium sulphate, the solvent was evaporated under reduced pressure, to give a pale yellow solid. Column chromatography on a silica gel using petroleum ether (boiling range 60°–80° C.) containing ethyl acetate (20% by volume), to give the desired compound as a white solid.

melting point: 159.8°–162° C.

$^1$H NMR δ (CDCl$_3$): 7.80 (2H,2×s); 7.00 (1H,s); 3.05 (3H,s)

EXAMPLE 10

This Example illustrates the preparation of 1-(2,6-dichloro-4-trifluoromethylphenyl)-2-methylsulphonyl-4-trifluoromethylpyrimidine-6-one (Compound No. 25 in Table I).

m-Chloroperbenzoic acid (0.24 g) was added to a stirred solution of 1-(2,6-dichloro-4-trifluoromethyl phenyl)-2-methylthio-4-trifluoromethylpyrimidin-6-one (the product of Example 8) (0.15 g) in chloroform (4 ml). After stirring for a period of 16 hours and allowing it to stand over a week-end, the reaction mixture was diluted with chloroform, and washed sequentially with aqueous sodium bicarbonate solution, aqueous sodium bisulphite solution and finally brine. After drying over anhydrous magnesium sulphate, the solvent was evaporated under reduced pressure to give a yellow solid. Titration with petroleum ether (boiling range 60°–80° C.) containing a small amount of ethyl acetate gave the desired compound as a white solid.

melting point: 191.7°–193.4° C.

$^1$H NMR δ (CDCl$_3$): 7.78 (2H,s); 7.11 (1H,s); 3.42 (3H,s)

EXAMPLE 11

This Example illustrates the preparation of 1-(2,6-dichloro-4-trifluoromethylphenyl)-2-amino-4-trifluoromethylpyrimidin-6-one (Compound No. 26 in Table I).

Excess gaseous ammonia was passed into a solution of 1-(2,6-dichloro-4-trifluoromethylphenyl)-2-methylsulphonyl-4-trifluoromethylpyrimidin-6-one (the product of Example 10) (0.130 g) in tertiary butanol (5 ml) at ambient temperature. After 1 hour, the solvent was evaporated, under reduced pressure to give a yellow solid, which was chromatographed on silica gel using petroleum ether (boiling range 60°–80° C.) containing ethyl acetate (20% by volume) as eluent to give the desired compound as a white crystalline solid.

$^1$H NMR (CDCl$_3$): 7.84 (2H,s); 6.43 (1H,s); 5.10 (2H, broad s)

EXAMPLE 12

The following compounds were prepared according to the general method of Example 11 from 1-(2,6- dichloro-4-trifluoromethylphenyl)-2-methylsulphonyl-4-trifluoromethyl pyrimidin-6-one (the product of Example 10) and the appropriate amine.

a) 1-(2,6-Dichloro-4-trifluoromethylphenyl)-2-methylamino-4-trifluoromethylpyrimidine-6-one (Compound No. 27 in Table I) was prepared using methylamine.

melting point: 211°–213.6° C.

$^1$H NMR δ (CDCl$_3$): 7.83 (2H,s); 6.35 (1H,s); 4.25 (1H,broad s); 3.00 (3H,d)

b) 1-(2,6-Dichloro-4-trifluoromethylphenyl)-2-dimethylamino-4-trifluoromethylpyrimidine-6-one (Compound No. 28 in Table I) was prepared using dimethyl amine.

melting point: 120°–125° C.

$^1$H NMR δ (CDCl$_3$): 7.75 (2H,s); 6.39 (1H,s); 2.80 (6H,s)

EXAMPLE 13

This Example illustrates the preparation of 1-(2,6-dichloro-4-trifluoromethylphenyl)-2-methyl-4-trifluoromethylpyrimidin-6-one (Compound No. 29 in Table I).

Acetyl chloride (0.71 g) and Hunigs base (0.26 g) were added to a solution of N-(2,6-dichloro-4-trifluoromethylphenyl)-3-amino-4,4,4-trifluorobut-2-en-1-amide (the product of preparation 17) (0.66 g) in dry toluene (8 ml). The reaction mixture was heated to 90° C. for a period of three hours, and then allowed to cool to ambient temperature. The reaction mixture was poured into water and then extracted with ethyl acetate, washed with water and dried over anhydrous magnesium sulphate. Evaporation of the solvent under reduced pressure gave a brown gum. The gum was subjected to column chromatography on silica gel using petroleum ether (boiling range 60°–80° C.) containing ethyl acetate (11% by volume) as eluent to give the desired compound as a waxy solid.

$^1$H NMR δ (CDCl$_3$): 7.83 (2H,s); 6.87 (1H,s); 2.26 (3H,s)

EXAMPLE 14

This example illustrates the preparation of 1-(2,6-dichloro-4-trifluoromethylphenyl)-4-trifluoromethylpyrimidin-6-thione (Compound No. 47 in Table 1).

Lawesson's Reagent (2,4-bis(4-methoxyphenyl)-1,3-dithia-2,4-diphosphetane-2,4-disulphide) (1 g) was added to a stirred solution of 1-(2,6-dichloro-4-trifluoromethylphenyl)-4-trifluoromethylpyrimidin-6-one (0.5 g) (EP 0338686) in dry, distilled pyridine (2.5 ml), and the reaction mixture was heated to 150° C. for 24 hours. After cooling to ambient temperature, the reaction mixture was dissolved in ethyl acetate and washed with brine. After drying over anhydrous magnesium sulphate, evaporation of the solvent under reduced pressure gave a brown oil. This material was subjected to medium pressure liquid chromatography, on a Gilson apparatus, using silica gel as the stationary phase, and eluting with hexane containing ethyl acetate (2% by volume). The appropriate fractions were collected to give the desired compound as a yellow oil which darkened on standing.

$^1$H NMR δ (CDCl$_3$): 8.02 (1H,s); 7.81 (2H,s); 7.70 (1H,s)

EXAMPLE 15

This example illustrates the preparation of 1-(2-chloro-6-nitro-4-trifluoromethylphenyl)-5-methylthio-4-trifluoromethylpyrimidin-6-one (Compound No. 31 in Table I).

Sodium hydride (0.46 g of 55% oil dispersion) was washed with hexane and suspended in anhydrous DMF (25 ml) and 5-methylthio-4-trifluoromethylpyrimidin-6-one (prepared according to Preparation 18) (2.00 g) was added in portions over 10 minutes, with stirring under nitrogen. The solution was stirred at room temperature for 20 minutes and 3-chloro-5-nitro-4-fluorobenzotrifluoride (4.60 g) was added dropwise. Stirring was continued for 2 hours, then the mixture was quenched with 2M HCl and extracted with ethyl acetate. The extracts were washed with water and brine, dried over magnesium sulphate and concentrated by evaporation of the solvent under reduced pressure. The residual oily solid was stirred with hexane and filtered to give 3.78 g of pale yellow solid.

melting point: 138.3°–141.2° C.

$^1$H NMR δ (CDCl$_3$): 8.45 (1H,d); 8.20 (1H,d) 8.00 (1H,s); 2.50 (3H,s)

EXAMPLE 16

1-(2,6-dichloro-4-trifluoromethylphenyl)-5-methylthio-4-trifluoromethylpyrimidin-6-one (Compound No. 30 of Table I) was similarly prepared according to Example 15 with the exception that it was carried out at 90° C.

melting point: 93.8°–96.2° C.

$^1$H NMR δ (CDCl$_3$): 7.90 (1H,s); 7.80 (2H,s); 2.55 (3H,s)

EXAMPLE 17

This example illustrates the preparation of 1-(2,6-dichloro-4-trifluoromethylphenyl)-5-methylsulphonyl-4-trifluoromethylpyrimidin-6-one (Compound No. 33 of Table I).

A solution of 1-(2,6-dichloro-4-trifluoromethylphenyl)-5-methylthio-4-trifluoromethylpyrimidin-6-one (Compound No. 30 of Table 1) (0.540 g) in dry chloroform (10 ml) was cooled to −15° C. and meta chloro perbenzoic acid (55%, 1 gm) was added in portions over 5 minutes with stirring. The mixture was stirred at −15° C. for 3½ hours, allowed to warm to room temperature and stirred for a further 16 hours.

The solution was diluted with more chloroform and washed successively with saturated sodium metabisulphite solution, saturated sodium bicarbonate solution and brine. The solution was then dried over magnesium sulphate and concentrated by evaporation of the solvent under reduced pressure to give 562 mg of a white solid product.

melting point: 190.8°–191.2° C.

$^1$H NMR δ (CDCl$_3$): 8.20 (1H,s); 7.85 (2H,s); 3.40 (3H,s)

EXAMPLE 18

This example illustrates the preparation of 1-(2-chloro-6-nitro-4-trifluoromethylphenyl)-5-methylsulphinyl-4-trifluoromethylpyrimidine-6-one (Compound No. 32 of Table I)

A solution of 1-(2-chloro-6-nitro-4-trifluoromethylphenyl)-5-methylthio-4-trifluoromethylpyrimidin-6-one (0.50 g) (Compound No. 31 in Table I) in dry chloroform (10 ml) was cooled to −15° C. and meta-chloro perbenzoic acid (55%, 0.40 g) was added with stirring. The mixture was stirred at −15° C. for 3½ hours and then washed successively with saturated sodium metabisulphite solution, saturated sodium bicarbonate solution and brine. The solution was then dried over magnesium sulphate and concentrated by evaporation of the solvent under reduced pressure. The residue was purified by HPLC (on silica gel using 70% ethyl acetate in hexane followed by 50% ethyl acetate in hexane) to give 247 mg of pale yellow solid.

melting point: 180.0°–180.8° C.

$^1$H NMR $\delta$ (CDCl$_3$): 8.50 (1H,s); 8.25 (2H,s); 3.10 (3H,d)

EXAMPLE 19

This example illustrates the preparation of 1-(2-chloro-6-nitro-4-trifluoromethylphenyl)-5-trifluoromethylthio-6-trifluoromethylpyrimidin-6-one (Compound No. 34 of Table I).

Trifluoromethylthio copper (0.35 g) was added to a solution of 1-(2-chloro-6-nitro-4-trifluoromethylphenyl)-5-bromo-4-trifluoromethylpyrimidin-6-one (0.50 g) (EP0338686) in anhydrous dimethylformamide (5 ml). The solution was heated under nitrogen at 90° C. for 2½ hours. Additional reagent (0.20 g) was added and heating was continued for a further 2 hours. The mixture was cooled, water and ethyl acetate were added and the insoluble residues removed. The layers were separated and the aqueous layer further extracted with ethyl acetate. The combined extracts were washed with water and brine, dried over magnesium sulphate and concentrated by evaporation of the solvent under reduced pressure to give a brown oil. The product (0.119 g) was isolated as an off-white solid by chromagraphy on silica (Merck 7729, eluted with 50–70% dichloromethane in hexane)

melting point: 150.4°–153.0° C.

$^1$H NMR $\delta$ (CDCl$_3$): 8.50 (1H,s); 8.25 (1H,s); 8.20 (1H,s)

The trifluoromethylthio copper was prepared according to Yagupolski. L. M. et al, Synthesis, 1975, page 721.

EXAMPLE 20

This example illustrates the preparation of 1-(2-chloro-6-nitro-4-trifluoromethylphenyl)-5-formyl-4-trifluoromethyl pyrimidin-6-one (Compound No. 35 of Table 1).

Sodium hydride (125 mg of 55% oil dispersion) was washed with hexane and suspended in anhydrous dimethylformamide (10 ml) and 5-formyl-4-trifluoromethylpyrimidin-6-one (prepared as in Preparation 19) (0.50 g) was added in portions over 5 minutes with stirring under nitrogen. After stirring for 30 minutes, 3-chloro-4-fluoro-5-nitro-benzotrifluoride (1.30 g) was added and the mixture was stirred at room temperature for 5 hours. The mixture was quenched with 2M hydrochloric acid and extracted with ethyl acetate. The extracts were washed with brine, dried over magnesium sulphate and concentrated by evaporation of the solvent under reduced pressure. The residual oil was triturated with ether/hexane to give the crude product. Purification by HPLC (silica; 30% ethyl acetate in hexane) followed by recrystallisation from ethyl acetate/hexane gave 238 mg of an off-white solid.

melting point: 151.3°–152.8° C.

$^1$H NMR $\delta$ (CDCl$_3$): 10.30 (1H,s); 8.50 (1H,s); 8.20 (2H,s)

EXAMPLE 21

This example illustrates the preparation of 1-(2-chloro-6-nitro-4-trifluoromethylphenyl)-5-difluoromethyl-4-trifluoromethylpyrimidin-6-one (Compound No. 38 of Table I).

1-(2-Chloro-6-nitro-4-trifluoromethylphenyl)-5-formyl-4-trifluoromethyl pyrimidin-6-one (100 mg) (Compound No. 35 of Table I) was added to a solution of diethylamino sulphur trifluoride (0.035 ml) in dry carbon tetrachloride (0.5 ml) with stirring under nitrogen, together with additional solvent (0.5 ml). After 2½ hours stirring at room temperature dry dichloromethane (1 ml) was added to produce a homogenous solution which was stirred for 2 hours and left overnight. Additional diethylamino sulphur trifluoride (5 drops) was added and after stirring for a further 1 hour the mixture was poured into water and extracted with dichloromethane. The extracts were washed with brine, dried over magnesium sulphate and concentrated by evaporation of the solvent under reduced pressure. The residual yellow oil was purified by HPLC (silica; 30% by volume of ethyl acetate in hexane) to give 48 mg of a white solid.

melting point: 137.5°–140° C.

$^1$H NMR $\delta$ (CDCl$_3$): 8.50(1H,s), 8.25(1H,s), 8.20(1H,s), 6.95(1H,t).

EXAMPLE 22

This example illustrates the preparation of 1-(2,6-dichloro-4-trifluoromethylphenyl)-5-ethoxy-4-trifluoromethylpyrimidin-6-one (Compound No. 36 of Table I).

Sodium hydride (0.162 g of 55% oil dispersion) was washed with hexane and suspended in dry dimethylformamide (15 ml). 5-Ethoxy-4-trifluoromethylpyrimidin-6-one (as prepared in Preparation 20) (0.70 g) was added in portions over 5 minutes with stirring under nitrogen. The mixture was stirred for 20 minutes and then 3,5-dichloro-4-fluorobenzotrifluoride (1.57 g) was added. The mixture was stirred at 70° C. for 7 hours then allowed to stand for two days. Further 3,5-dichloro-4-fluorobenzotrifluoride (1.57 g) was added and the mixture heated at 100° C. for 24 hours. The mixture was cooled and poured into 2M hydrochloric acid and extracted with ethyl acetate. The extracts were washed with water and brine, dried over magnesium sulphate and concentrated by evaporation of the solvent under reduced pressure. The residual brown oil was purified by HPLC (silica; 20% ethyl acetate in hexane) to give 244 mg of an off-white solid.

melting point: 70.5°–73° C.

$^1$H NMR $\delta$ (CDCl$_3$): 7.85(2H,s); 7.75(1H,s); 4.45(2H,q); 1.40(3H,t)

EXAMPLE 23

1-(2-Chloro-6-nitro-4-trifluoromethylphenyl)-5-ethoxy-4-trifluoromethylpyrimidin-6-one (Compound No. 37 of Table I) (65 mg) was also isolated from the HPLC purification of Example 22. This product was derived from 3-chloro-5-nitro-4-fluoro-benzotrifluoride which was present as an impurity in the reagent used.

melting point: 97.5°–100.5° C.

$^1$H NMR $\delta$ (CDCl$_3$): 8.45 (1H,s); 8.20(1H,s); 7.80(1H,s); 4.40(2H,q); 1.40(3H,t)

EXAMPLE 24

This example illustrates the preparation of 1-(2-chloro-6-nitro-4-trifluoromethylphenyl)-5-methyl-4-trifluoromethyl pyrimidin-6-one (Compound No. 40 of Table 1).

Sodium hydride (0.40 g of 55% oil dispersion) was washed with hexane and suspended in anhydrous dimethylformamide (30 ml). 5-methyl-4-trifluoromethylpyrimidin-6-one (prepared according to Preparation 21) (1.50 g) was added in portions with stirring under nitrogen. When a clear solution was obtained 3-chloro-4-fluoro-5-nitro-benzotrifluoride (4.10 g) was added dropwise and the solution stirred for 6 hours at room temperature. The mixture was poured into water, acidified and extracted with ethyl acetate. The extracts were washed with water, dried over magnesium sulphate and concentrated by evaporation of the solvent under reduced pressure. The residue was stirred with petroleum ether (boiling range 30°–40° C.) and 2.77 g of a buff crystalline solid was collected.

melting point: 156.2°–157.7° C.

$^1$H NMR (CDCl$_3$): 8.40 (1H,s); 8.20 (1H,s); 7.95 (1H,s); 2.30 (3H,s)

EXAMPLE 25

1-(2,6-Dichloro-4-trifluoromethylphenyl)-5-methyl-4-trifluoromethyl-pyrimidin-6-one (Compound No. 39 of Table I) was similarly prepared according to Example 24 with the exception that the reaction was heated at 90° C.

melting point: 156.3°–157.6° C.

$^1$H NMR δ (CDCl$_3$): 7.80 (2H,s); 7.88 (1H,s); 2.35 (3H,s)

EXAMPLE 26

This example illustrates the preparation of 1-(2,6-dichloro-4-trifluoromethylphenyl)-5-amino-4-trifluoromethylpyrimidin-6-one (Compound No. 41 of Table I).

Sodium hydride (0.142 g of 55% oil dispersion was washed with hexane and suspended in dry dimethylformamide (20 ml). 5-Amino-4-trifluoromethylpyrimidin-6-one (0.53 g) was added with stirring under nitrogen. When a clear solution was obtained, 3,5-dichloro-4-fluorobenzotrifluoride (1.38 g) was added dropwise. The mixture was stirred at room temperature for 2 hours and allowed to stand for 2 days. The mixture was poured into water and extracted with ethyl acetate. The extracts were washed with water and brine, dried over magnesium sulphate and concentrated by evaporation of the solvent under reduced pressure. The residue was dissolved in 35% by volume of ethyl acetate in hexane and some insoluble residues removed. The filtrate was purified by HPLC (silica) using the same solvents. The still impure product was washed with hexane and subjected to a second HPLC stage (20% ethyl acetate in hexane) and again washed with hexane to give an off-white solid product.

melting point: 163.0°–163.5° C.

$^1$H NMR δ (CDCl$_3$): 7.8 (2H,s); 7.4 (1H,s); 5.05 (2H, broad s)

The 5-amino-4-trifluoromethylpyrimidin-6-one used in this example was obtained by the method of A. Giner-Sorolla and A Bendick, Journal of American Chemical Society, 80, 5744, 1958.

EXAMPLE 27

This example illustrates the preparation of 1-(2,6-dichloro-4-trifluoromethylthiophenyl)-4-trifluoromethyl pyrimidin-6-one (Compound No. 43 of Table I).

Trifluoromethylthio copper (0.9 g) was added to a solution of 1-(2,6-dichloro-4-iodophenyl)-4-trifluoromethyl pyrimidin-6-one (Compound 4 of Table I as prepared in Example 4) (0.6 g) in anhydrous DMF (10 ml). The mixture was stirred under nitrogen and heated at 100° C. for 8½ hours. Additional trifluoromethylthio copper (0.4 g) was added and the mixture was heated at 100° C. for a further 11½ hours.

The mixture was cooled, diluted with water and ethyl acetate and filtered. The layers were separated and the aqueous phase extracted with ethyl acetate. The combined extracts were washed with water and brine, dried over magnesium sulphate and concentrated by evaporation of the solvent under reduced pressure. The residue was stirred with ether and decanted from a residual insoluble brown gum. Removal of the ether gave 883 mg of a yellow solid.

Purification by HPLC (silica; 20% ethyl acetate in hexane followed by 15% ethyl acetate in hexane) gave 170 mg of a white solid.

melting point: 113°–114.3° C.

$^1$H NMR δ (CDCl$_3$): 8.00 (1H,s); 7.0 (1H,s); 7.85 (2H,s)

The trifluoromethylthio copper was prepared according to Yagupolski L. M., et al, Synthesis, 1975, 721.

EXAMPLE 28

This example illustrates the preparation of 1-(2-chloro-6-nitro-4-trifluoromethylphenyl)-5-hydroxymethyl-4-trifluoromethylpyrimidin-6-one (Compound No. 45 of Table I).

Sodium hydride (50 mg of 55% oil dispersion) was washed with hexane and suspended in dry dimethylformamide (5 ml). 5-hydroxymethyl-4-trifluoromethylpyrimidin-6-one (200 mg) (as prepared in Preparation 23) was added in portions over a period of 5 minutes, with stirring under nitrogen. After stirring for 30 minutes, 3-chloro-4-fluoro-5-nitro-benzotrifluoride (500 mg) was added and stirring was continued for 1 hour. The mixture was quenched with 2M HCl and extracted with ethyl acetate. The extracts were washed with water and brine, dried over magnesium sulphate and concentrated by evaporation of the solvent under reduced pressure to give a light yellow oil. The oil was purified by chromatography (Merck 7729, silica with 20–40% by volume of ethyl acetate in hexane as eluent), to give an off-white solid (314 mg).

melting point: 117.4°–119.6° C.

$^1$H NMR δ (CDCl$_3$): 8.45 (1H,s); 8.25 (1H,s); 8.10 (1H,s); 4.75 (2H,d); 3.0 (1H,t)

EXAMPLE 29

This example illustrates the preparation of 1-(2,6-dichloro-4-trifluoromethylphenyl)-5-(1-hydroxyethyl)-4-trifluoromethylpyrimidin-6-one (Compound No. 46 of Table I).

Sodium hydride (70 mg of 55% oil dispersion) was washed with hexane and suspended in dry dimethylformamide. 5-(1-hydroxyethyl)-4-trifluoromethylpyrimidin-6-one (300 mg) (as prepared in Preparation 24) was added in portions over a period of 5 minutes, with stirring under nitrogen. After stirring for a further 30 minutes 3,5-dichloro-4-fluorobenzotrifluoride (672 mg) was added to the reaction mixture. The mixture was stirred at room temperature for 1 hour and then heated to 80° C. for 40 hours. The mixture was cooled, quenched with 2M HCl and extracted with ethyl acetate. The extracts were washed with brine, dried over magnesium sulphate and concentrated by evaporation of the solvent under reduced pressure to give a yellow oil. The oil was purified by chromatography (Merck silica 7729 using 20% by volume of ethyl acetate in hexane as eluent), to give a yellow gum which on trituration with hexane gave a white solid (82 mg).

melting point: 106.5°–108.4° C.

$^1$H NMR δ (CDCl$_3$): 7.85 (2H,s); 7.95 (1H,s); 1.6 (3H,d); 4.11 (1H,d); 5.12 (1H,m)

EXAMPLE 30

This example illustrates the preparation of 1-(2-chloro-6-nitro-4-trifluoromethylphenyl)-5-nitro-4-trifluoromethylpyrimidin-6-one (Compound No. 42 of Table 1).

The title compound was prepared by reaction of 1-(2-chloro-6-nitro-4-trifluoromethylphenyl)-4-trifluoromethylpyrimidin-6-one (EP 0338686) with nitronium tetrafluoroborate in tetramethylene sulphone solution at 150° C. The compound was identified by mass spectrometry.

electron impact, m/e: 432 (1xCl,M+), 397 (base peak,M+-Cl), 386 (M+-NO$_2$), 351, 340, 313, 223, 193, 187, 160, 143, 121.

EXAMPLE 31

This example illustrates the preparation of 1-(3-chloro-5-nitro-4-trifluoromethylphenyl)-5-(1-fluoroethyl)-4-trifluoromethylpyrimidin-6-one (Compound No. 48 of Table I).

Diethylamino sulphur trifluoride (0.043 ml) in chloroform (2 ml) was added over 10 minutes to a solution of 1-(3-chloro-5-nitro-4-trifluoromethylphenyl)-5-(1-hydroxyethyl)-4-trifluoromethylpyrimidin-6-one (128 mg) in chloroform (2 ml) with stirring at −50° C. under nitrogen. The solution was allowed to warm to room temperature over 40 minutes and allowed to stand overnight. The solution was diluted with dichloromethane, washed with water and brine, dried over magnesium sulphate and concentrated by evaporation of the solvent under reduced pressure to give a yellow oil. The oil was purified by chromatography (Merck 7729 silica using 50–90% dichloromethane in hexane) to give a white solid (53 mg).

melting point: 127.3°–129.8° C.

$^1$H NMR δ (CDCl$_3$): 8.45 (1H,s); 8.20 (1H,s); 8.10 (1H,s); 5.90 (1H,m); 170 (3H,m)

The 1-(3-chloro-5-nitro-4-trifluoromethylphenyl)-5-(1-hydroxyethyl)-4-trifluoromethylpyrimidin-6-one used in this example was prepared using the general method of Example 28.

$^1$H NMR δ (CDCl$_3$): 8.45 (1H,s); 8.25 (1H,s); 8.05 (1H,s); 1.60 (3H,d); 5.10 (1H,m); 3.90 (1H,m)

EXAMPLE 32

The activity of the compounds of formula (I) was determined using a variety of pests. The pests were treated with a liquid composition usually containing 500 parts per million (ppm) by weight of the compound. The compositions were made by dissolving the compound in acetone and diluting the solutions with water containing 0.01% by weight of a wetting agent sold under the trade name "SYNPERONIC" NX until the liquid composition contained the required concentration of the compound. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

The results of the tests are presented in Table III for each of the compounds at the rate in parts per million given in the second column. The results indicate a grading of mortality designated as 9, 5 or 0 wherein 9 indicates 80–100% mortality, 5 indicates 50–79% mortality and 0 indicates less than 50% mortality. Information regarding the pest species, the support medium or food, and the type and duration of the test is given in Table II. The pest species is designated by a letter code.

TABLE II

| CODE LETTERS (TABLE III) | TEST SPECIES | SUPPORT MEDIUM/FOOD | TYPE OF TEST | DURATION (DAYS) |
|---|---|---|---|---|
| BG | Blattella germanica (Cockroach nymphs) | Plastic pot | Residual | 3 |
| MD | Musca domestica (houseflies - adults) | Cotton wool/sugar | Contact | 1 |
| HV | Heliothis virescens (tobacco budworm-larvae) | Cotton leaf | Residual | 2 |
| SP | Spodoptera exigua (lesser armyworm-larvae) | Cotton leaf | Residual | 2 |

"Contact" test indicates that both pests and medium were treated and "Residual" test indicates that the medium was treated before infestation with the pests.

TABLE III

| COMPOUND | RATE OF APPLICATION (ppm) | MD | BG | HV | SP |
|---|---|---|---|---|---|
| | | \multicolumn{4}{c}{(see Table II)} | | | |
| 1 | 500 | 9 | 5 | 0 | 5 |
| 2 | 500 | 9 | 5 | 0 | 5 |
| 3 | 500 | 5 | 0 | 0 | 5 |
| 4 | 500 | 9 | 0 | 9 | 0 |
| 5 | 500 | 9 | 0 | 0 | 0 |
| 6 | 500 | 9 | 0 | 0 | 9 |
| 7 | 500 | 9 | 0 | — | — |
| 8 | 500 | 9 | 9 | 0 | 0 |
| 9 | 500 | 9 | 9 | 9 | 5 |
| 10 | 500 | 0 | 9 | 0 | 0 |
| 11 | 500 | 9 | 0 | 0 | 0 |
| 12 | 500 | 0 | 9 | 0 | 0 |
| 13 | 100 | 5 | 9 | — | — |
| 14 | 500 | 9 | 9 | 9 | 9 |
| 15 | 500 | 9 | 9 | 0 | 0 |
| 16 | 500 | 9 | 9 | 0 | 0 |
| 17 | 500 | 9 | 9 | 0 | 0 |
| 18 | 500 | 9 | 9 | 5 | 0 |
| 19 | 500 | 9 | 9 | 0 | 9 |
| 20 | 500 | 9 | 9 | 0 | 0 |
| 21 | 500 | 9 | 9 | 0 | 0 |
| 22 | 500 | 9 | 9 | 9 | 0 |
| 23 | 500 | 9 | 9 | 0 | 0 |
| 24 | 500 | 9 | 0 | 0 | 0 |
| 25 | 500 | 9 | 0 | 0 | 0 |
| 26 | 500 | 9 | 9 | 9 | 0 |
| 28 | 500 | 9 | 5 | 0 | 0 |
| 29 | 500 | 9 | 9 | 9 | 0 |
| 30 | 500 | 9 | 9 | 9 | 9 |
| 31 | 500 | 9 | 0 | 0 | 0 |

TABLE III-continued

| COMPOUND | RATE OF APPLICATION (ppm) | SPECIES | | | |
|---|---|---|---|---|---|
| | | MD | BG | HV | SP |
| | | (see Table II) | | | |
| 32 | 500 | 9 | 0 | 0 | 0 |
| 33 | 500 | 9 | 0 | 0 | 0 |
| 34 | 500 | 9 | 5 | 0 | 5 |
| 35 | 500 | 9 | 0 | 0 | 0 |
| 36 | 500 | 9 | 9 | 0 | 0 |
| 37 | 100 | 5 | 0 | 0 | 0 |
| 39 | 500 | 9 | 9 | 0 | 0 |
| 40 | 500 | 9 | 9 | 0 | 0 |
| 43 | 500 | 9 | 9 | 0 | 9 |
| 47 | 500 | 9 | 9 | 9 | 0 |

— = not tested

EXAMPLES 33-51

Examples 33-51 illustrate formulations suitable for the application of compounds according to the invention. In the examples, the following ingredients are referred to by their Registered Trade Marks and have the composition as shown below.

| Registered Trade Mark | Composition |
|---|---|
| Synperonic NP8 | Nonylphenol-ethylene oxide condensate |
| Synperonic NP13 | |
| Synperonic OP10 | |
| Aromasol H | Alkylbenzene solvent |
| Solvesso 200 | Inert organic diluent |
| Keltrol | Polysaccharide |

EXAMPLE 33

This example illustrates an emulsifiable concentrate composition which is readily convertible by dilution with water into a liquid preparation suitable for spraying purposes. The concentrate has the following composition:

| | % Weight |
|---|---|
| Compound | 25.0 |
| SYNPERONIC NP13 | 2.5 |
| Calcium dodecylbenzenenesulphonate | 2.5 |
| Methylcyclohexanone | 70 |

EXAMPLE 34

This example illustrates an emulsifiable concentrate composition which is readily convertible by dilution with water into a liquid preparation suitable for spraying purposes. The concentrate has the following composition:

| | % Weight |
|---|---|
| Compound | 10.0 |
| SYNPERONIC NP13 | 4.0 |
| Calcium dodecylbenzenesulphonate | 6.0 |
| AROMASOL H | 50.0 |
| Methylcyclohexanone | 30.0 |

EXAMPLE 35

This Example illustrates a wettable powder composition which is readily convertible by dilution with water into a liquid preparation suitable for spraying purposes. The wettable powder has the following composition:

| | % Weight |
|---|---|
| Compound | 10.0 |
| Silica | 5.0 |
| Sodium lignosulphonate | 5.0 |
| Sodium lauryl sulphate | 4.0 |
| Kaolinite | 76.0 |

EXAMPLE 36

This Example illustrates a wettable powder composition which is readily convertible by dilution with water into a liquid preparation suitable for spraying purposes. The wettable powder has the following composition:

| | % Weight |
|---|---|
| Compound | 1.0 |
| Sodium lignosulphonate | 5.0 |
| Sodium lauryl sulphate | 2.0 |
| Kaolinite | 92.0 |

EXAMPLE 37

This Example illustrates a wettable powder composition which is readily convertible by dilution with water into a liquid preparation suitable for spraying purposes. The wettable powder has the following composition:

| | % Weight |
|---|---|
| Compound | 40.0 |
| Silica | 20.0 |
| Calcium lignosulphonate | 5.0 |
| Sodium lauryl sulphate | 2.0 |
| Kaolinite | 33.0 |

EXAMPLE 38

This Example illustrates a dusting powder which may be applied directly to plants or other surfaces and comprises 1% by weight of the compound of the invention, 2% by weight of silica and 97% by weight of talc.

EXAMPLE 39

This Example illustrates a concentrated liquid formulation suitable for application by ultra low volume techniques after mixing with paraffinic diluents.

| | % Weight |
|---|---|
| Compound | 25.0 |
| N-methyl-2-pyrollidone | 50.0 |
| SOLVESSO 200 | 25.0 |

EXAMPLE 40

This Example illustrates a concentrated liquid formulation suitable for application by ultra low volume techniques after mixing with paraffinic diluents.

| | % Weight |
|---|---|
| Compound | 10.0 |
| N-methyl-2-pyrollidone | 20.0 |
| SOLVESSO 200 | 70.0 |

EXAMPLE 41

This Example illustrates a liquid formulation suitable for application (undiluted) by ultra low volume techniques.

|  | % Weight |
| --- | --- |
| Compound | 10 |
| Cotton seed oil | 50 |
| Butyldiethoxol acetate | 40 |

EXAMPLE 42

This Example illustrates a capsule suspension concentrate which is readily convertible by dilution with water to form a preparation suitable for application as an aqueous spray.

|  | % Weight |
| --- | --- |
| Compound | 10.0 |
| Toluene di-isocyanate | 3.0 |
| Ethylenediamine | 2.0 |
| Polyvinyl alcohol | 2.0 |
| Bentonite | 1.5 |
| Di-hydroisopharone | 30.0 |
| Solvesso 200 | 10.0 |
| Polysaccharide (e.g. KELTROL) | 0.1 |
| Water | 41.4 |

EXAMPLE 43

This Example illustrates a capsule suspension concentrate which is readily convertible by dilution with water to form a preparation suitable for application as an aqueous spray.

|  | % Weight |
| --- | --- |
| Compound | 1.0 |
| Toluene di-isocyanate | 3.0 |
| Ethylenediamine | 2.0 |
| Polyvinyl alcohol | 2.0 |
| Bentonite | 1.5 |
| Di-hydroisopharone | 5.0 |
| Solvesso 200 | 2.0 |
| Polysaccharide (e.g. KELTROL) | 0.1 |
| Water | 83.4 |

EXAMPLE 44

This Example illustrates a ready for use granular formulation:

|  | % Weight |
| --- | --- |
| Compound | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 45

This Example illustrates an aqueous suspension concentrate:

|  | % Weight |
| --- | --- |
| Compound | 50.0 |
| Kaolinite | 15.0 |
| Sodium lignosulphonate | 3.0 |
| nonylphenolethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 18.3 |

EXAMPLE 46

This Example illustrates a ready for use dust (D.P.) made from a concentrate:

|  | % Weight |
| --- | --- |
| Concentrate: |  |
| Compound | 10 |
| Silica | 20 |
| Magnesium Carbonate | 70 |
| Dust Example containing 1% active ingredient: |  |
| Above concentrate | 10 |
| Talc | 90 |

EXAMPLE 47

This Example illustrates a ready for use granule formulation:

|  | % Weight |
| --- | --- |
| Compound | 5 |
| Synperonic NP8 | 2 |
| Pumice granules (20/40 BS Mesh) | 93 |

EXAMPLE 48

This example illustrates a water dispersible granule formulation.

|  | % Weight |
| --- | --- |
| Compound | 50 |
| Silica | 5 |
| Sodium lignosulphate | 10 |
| Sodium dioctylsulphosuccinate | 5 |
| Sodium acetate | 10 |
| Montmorillonite powder | 20 |

EXAMPLE 49

This Example illustrates an emulsifiable concentrate which is diluteable in water to form a liquid composition for spraying.

|  | % Weight |
| --- | --- |
| Compound | 50.0 |
| Span 40 | 0.8 |
| Tween 40 | 8.0 |
| Di-hydroisopharone | 30.0 |
| Solvesso 100 | 25.0 |
| Water | 31.2 |

EXAMPLE 50

This Example illustrates an aerosol concentrate.

|  | % Weight |
|---|---|
| Compound | 1.0 |
| Methyl-isobutylketone | 50.0 |
| Solvesso 100 | 94.0 |

EXAMPLE 51

This Example illustrates an aerosol composition.

|  | % Weight |
|---|---|
| Aerosol concentrate (Example 50) | 5.0 |
| Colourless kerosene | 25.0 |
| Methylene chloride | 10.0 |
| Propellant* | 60.0 |

*(Hydrocarbon aerosol propellant, pressure 40–80 psig)

We claim:

1. A compound of formula (I):

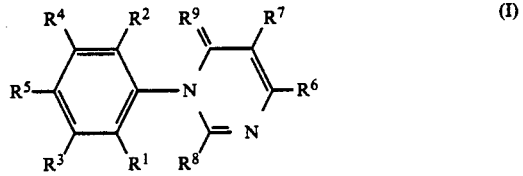

wherein $R^1$ and $R^2$ are independently selected from hydrogen, halogen, haloalkyl, alkoxy or nitro, provided that $R^1$ and $R^2$ are not both nitro; $R^3$ and $R^4$ are independently selected from hydrogen, halogen, alkyl or cycloalkyl; $R^5$ is halogen, nitro, haloalkyl, haloalkoxy or $-S(O)_nR^{10}$; $R^6$ is halogen, nitro, haloalkyl, haloalkoxy or $-S(O)_nR^{10}$; $R^7$ is hydrogen, alkyl, halogen, hydroxyalkyl, cyano, nitro, alkoxy, $-S(O)_nR^{10}$, $NR^{11}R^{12}$, haloalkyl or formyl; $R^8$ is hydrogen, halogen, $NR^{11}R^{12}$, alkyl, cycloalkyl or $S(O)_nR^{10}$; and $R^9$ is oxygen or sulphur; where n is 0, 1 or 2; and $R^{10}$ is alkyl, haloalkyl or cycloalkyl; and $R^{11}$ and $R^{12}$ are independently selected from hydrogen, alkyl or cycloalkyl; provided that when $R^5$ is trifluoromethyl at least one of the following applies:

(i) $R^1$ or $R^2$ is haloalkyl or alkoxy;
(ii) $R^3$ or $R^4$ are alkyl or cycloalkyl;
(iii) $R^6$ is haloalkoxy, nitro or $-S(O)_nR^{10}$;
(iv) $R^7$ is alkyl, nitro, hydroxyalkyl, alkoxy, $S(O)_nR^{10}$, $NR^{11}R^{12}$, formyl or haloalkyl;
(v) $R^8$ is other than hydrogen;
(vi) $R^9$ is sulphur; and further provided that (a) $R^1$, $R^2$, $R^3$ and $R^4$ are not all fluorine and (b) when $R^5$ is chlorine, $R^1$ and $R^2$ are both halogen; the alkyl and haloalkyl including up to 6 carbons, the cycloalkyl including from 3 to 10 carbons and the alkoxy, hydroxyalkyl and haloalkoxy including up to 4 carbons.

2. A compound according to claim 1 wherein $R^3$ and $R^4$ are independently selected from hydrogen or methyl.

3. A compound according to claims 1 or 2 wherein $R^1$ and $R^2$ are independently selected from fluorine, chlorine, bromine, nitro, trifluoromethyl or methoxy.

4. A compound according to claim 1 wherein $R^5$ is selected from trifluoromethyl, pentafluoroethyl, $S(O)_nR^{10}$, iodine, bromine, chlorine or trifluoromethoxy.

5. A compound according to claim 1 wherein $R^7$ is selected from hydrogen, trifluoromethylthio, methylthio or methyl.

6. A compound according to claim 1 wherein $R^8$ is selected from hydrogen, methyl, $NH_2$ or methylthio.

7. A compound according to claim 1 wherein $R^6$ is trifluoromethyl or pentafluoroethyl.

8. A compound according to claim 1 wherein $R^1$ and $R^2$ are both halogen, $R^3$ and $R^4$ are both hydrogen, $R^5$ and $R^6$ are both independently trifluoromethyl or pentafluoroethyl, $R^7$ is hydrogen or halogen and $R^8$ is hydrogen, $NH_2$ or methyl.

9. A compound according to claim 8 wherein $R^1$ and $R^2$ are both halogen, $R^3$ and $R^4$ are both hydrogen, $R^5$ is pentafluoroethyl, $R^6$ is trifluoromethyl or pentafluoroethyl, $R^7$ is hydrogen and $R^8$ is hydrogen.

10. A compound according to claim 1 wherein $R^1$ is halogen, $R^2$ is nitro, $R^3$ and $R^4$ are both hydrogen, $R^5$ is pentafluoroethyl, $R^6$ is trifluoromethyl or pentafluoroethyl, $R^7$ and $R^8$ are both hydrogen.

11. A compound according to claim 1 wherein $R^1$ is halogen, $R^2$ is halogen or nitro, R3 and R4 are both hydrogen, $R^5$ is trifluoromethyoxy or trifluoromethylthio, $R^6$ is trifluoromethyl or pentafluoroethyl, $R^7$ is hydrogen or halogen, $R^8$ is hydrogen.

12. A compound according to claim 1 wherein $R^1$ and $R^2$ are both halogen, $R^3$ and $R^4$ are both hydrogen, $R^5$ and $R^6$ are both independently trifluoromethyl, trifluoromethoxy or pentafluoroethyl, $R^7$ is hydrogen or halogen, $R^8$ is hydrogen and $R^9$ is sulphur.

13. A compound according to claim 1 wherein $R^1$ and $R^2$ are both halogen, $R^3$ and $R^4$ are both hydrogen, $R^5$ is trifluoromethylthio, $R^6$ is trifluoromethyl or pentafluoroethyl, $R^7$ is hydrogen or halogen, $R^8$ is hydrogen and $R^9$ is sulphur.

14. A method of killing or controlling insect or acarine pests which method comprises applying to the pest or to a locus thereof an effective amount of a compound of formula (I) as defined in claim 1.

15. An insecticidal or acaricidal composition comprising an effective amount of a compound of formula (I) as defined in claim 1 in combination with a diluent or carrier.

16. Compounds of formula (IV):

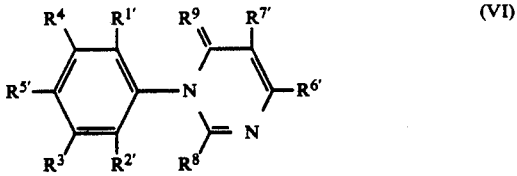

wherein $R^3$, $R^4$, $R^8$ and $R^9$ are as defined in claim 1 and $R^{1'}$, $R^{2'}$, $R^{5'}$, $R^{6'}$ and $R^{7'}$ are amino or are equivalent to $R^1$, $R^2$, $R^5$, $R^6$ and $R^7$ as defined in claim 1 respectively, provided that at least one of $R^{1'}$, $R^{2'}$, $R^{5'}$, $R^{6'}$ or $R^{7'}$ is amino.

* * * * *